(12) United States Patent
Yabe et al.

(10) Patent No.: US 10,314,468 B2
(45) Date of Patent: Jun. 11, 2019

(54) LIGHT SOURCE APPARATUS

(71) Applicant: OLYMPUS CORPORATION, Tokyo (JP)

(72) Inventors: Yusuke Yabe, Chofu (JP); Hiroyuki Kamee, Koganei (JP); Takeshi Ito, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/614,751

(22) Filed: Jun. 6, 2017

(65) Prior Publication Data
US 2017/0265733 A1    Sep. 21, 2017

Related U.S. Application Data

(63) Continuation of application No. PCT/JP2016/052891, filed on Feb. 1, 2016.

(30) Foreign Application Priority Data

May 28, 2015 (JP) .................................. 2015-109051

(51) Int. Cl.
*A61B 1/06*    (2006.01)
*A61B 1/00*    (2006.01)
(Continued)

(52) U.S. Cl.
CPC .............. *A61B 1/0638* (2013.01); *A61B 1/00* (2013.01); *A61B 1/00009* (2013.01); *A61B 1/06* (2013.01);
(Continued)

(58) Field of Classification Search
CPC . A61B 1/0638; A61B 1/00009; A61B 1/0669; A61B 1/0684; A61B 1/06;
(Continued)

(56) References Cited

U.S. PATENT DOCUMENTS 6,602,186 B1 * 8/2003 Sugimoto .......... A61B 1/00009
                                                           600/126
2010/0084563 A1    4/2010 Ohno
(Continued)

FOREIGN PATENT DOCUMENTS

CN         102445814 A      5/2012
EP           2514352 A1    10/2012
(Continued)

OTHER PUBLICATIONS

International Search Report dated Apr. 26, 2016 issued in PCT/JP2016/052891.
(Continued)

*Primary Examiner* — Anh T Mai
*Assistant Examiner* — Jessica M Apenteng
(74) *Attorney, Agent, or Firm* — Scully, Scott, Murphy & Presser, P.C.

(57) ABSTRACT

A light source apparatus, capable of supplying white light including a predetermined wavelength band and a special light, which is light including the predetermined wavelength band and narrower in a band than the white light, includes: a first light source configured to emit light in a first wavelength band including the predetermined wavelength band, a second light source configured to emit light in a second wavelength band including the predetermined wavelength band, and a dichroic mirror configured to selectively transmit light in the predetermined wavelength band from one light of the lights in the first and second wavelength bands, selectively reflect light in a third wavelength band other than the predetermined wavelength band from the other light of the lights in the first and second wavelength bands, and mix and emit the light in the predetermined wavelength band and the light in the third wavelength band.

5 Claims, 16 Drawing Sheets

(51) Int. Cl.
*G02B 23/24* (2006.01)
*G02B 19/00* (2006.01)
*G02B 27/14* (2006.01)

(52) U.S. Cl.
CPC ......... *G02B 23/24* (2013.01); *G02B 23/2461* (2013.01); *A61B 1/0669* (2013.01); *A61B 1/0684* (2013.01); *G02B 19/0061* (2013.01); *G02B 27/141* (2013.01)

(58) Field of Classification Search
CPC .. A61B 1/00; G02B 23/2461; G02B 19/0061; G02B 27/141; G02B 23/24
USPC ....................................................... 362/615
See application file for complete search history.

(56) References Cited

U.S. PATENT DOCUMENTS

| | | |
|---|---|---|
| 2012/0082446 A1 | 4/2012 | Kumai |
| 2012/0271103 A1 | 10/2012 | Gono et al. |
| 2013/0113911 A1 | 5/2013 | Hanano et al. |
| 2015/0094530 A1* | 4/2015 | Moriya ................ G02B 6/0001 600/103 |

FOREIGN PATENT DOCUMENTS

| | | |
|---|---|---|
| EP | 3 111 822 A1 | 1/2017 |
| JP | 5198694 B2 | 5/2013 |
| WO | WO 2012/056860 A1 | 5/2012 |

OTHER PUBLICATIONS

Extended Supplementary European Search Report dated Jul. 24, 2018 in European Patent Application No. 16 79 9601.6.

\* cited by examiner

LIGHT SOURCE APPARATUS

CROSS REFERENCE TO RELATED APPLICATION

This application is a continuation application of PCT/JP2016/052891 filed on Feb. 1, 2016 and claims benefit of Japanese Application No. 2015-109051 filed in Japan on May 28, 2015, the entire contents of which are incorporated herein by this reference.

BACKGROUND OF INVENTION

1. Field of the Invention

The present invention relates to a light source apparatus and, more particularly, to a light source apparatus used for illumination of an object present in a body cavity of a subject.

2. Description of the Related Art

In an endoscopic observation in a medical field, for example, a white light observation has been performed that is capable of displaying, by irradiating an object such as a biological tissue present in a body cavity of a subject with white light, an observation image having visibility substantially the same as visibility of the object viewed by naked eyes.

In the endoscopic observation in the medical field, for example, a special light observation has been performed that is capable of displaying, by irradiating a biological tissue present in a body cavity of a subject with special light, which is light subjected to band limitation according to a characteristic of a predetermined target object included in the biological tissue, an observation image having improved visibility of the predetermined target object compared with the white light observation.

For example, Japanese Patent No. 5198694 discloses, in an endoscope system, a configuration capable of selecting a desired observation mode among three observation modes of a normal observation mode for displaying a normal observation image obtained by a normal observation equivalent to the white light observation, a narrow band observation mode for displaying a narrow band observation image obtained by a narrow band observation included in one kind of the special light observation, and a twin mode for simultaneously displaying the normal observation image and the narrow band observation image.

SUMMARY OF THE INVENTION

A light source apparatus according to an aspect of the present invention is a light source apparatus capable of supplying, as illumination light for illuminating an object, white light including a predetermined wavelength band and a special light, which is light including the predetermined wavelength band and narrower in a band than the white light. The light source apparatus includes: a first light source configured to emit light in a first wavelength band including the predetermined wavelength band; a second light source configured to emit light in a second wavelength band including the predetermined wavelength band; and a dichroic mirror configured to selectively transmit light in the predetermined wavelength band from one light of the light in the first wavelength band and the light in the second wavelength band, selectively reflect light in a third wavelength band, which is light in a wavelength band other than the predetermined wavelength band, from another light of the light in the first wavelength band and the light in the second wavelength band, and mix and emit the light in the predetermined wavelength band and the light in the third wavelength band.

DETAILED DESCRIPTION OF THE PREFERRED EMBODIMENT(S)

Embodiments of the present invention are explained below with reference to the drawings.

First Embodiment

FIG. 1 to FIG. 5 relate to a first embodiment of the present invention.

Figure 1:
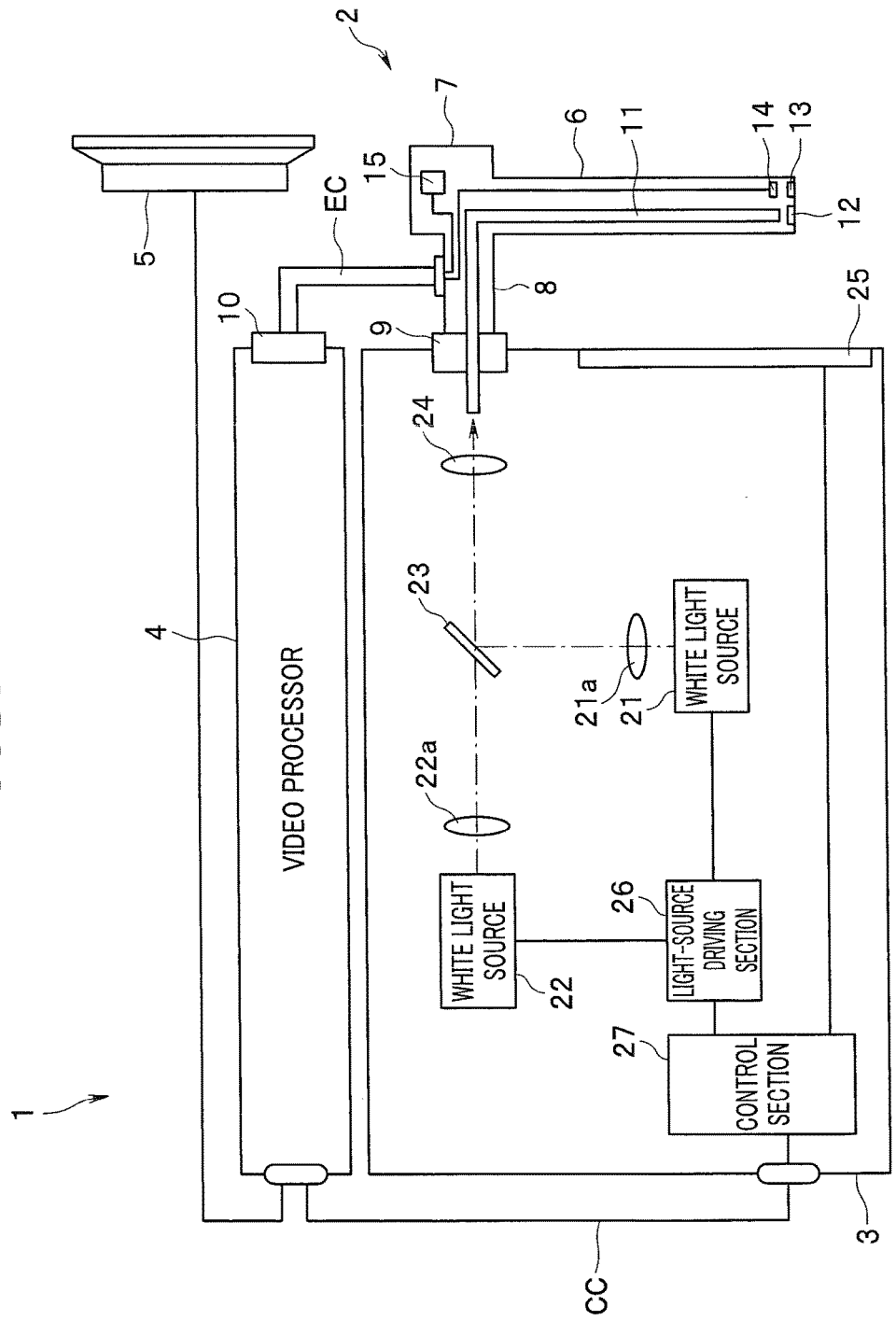
FIG. 1 is a diagram showing a configuration of a main part of an endoscope system including a light source apparatus according to a first embodiment.

An endoscope system 1 includes, as shown in FIG. 1, an endoscope 2 configured to pick up an image of an object such as a biological tissue present in a body cavity of a subject and output an image pickup signal, a light source apparatus 3 configured to supply illumination light for illuminating the object to the endoscope 2, a video processor 4 configured to generate and output an observation image corresponding to the image pickup signal outputted from the endoscope 2, and a monitor 5 configured to display the observation image and the like outputted from the video processor 4. The light source apparatus 3 and the video processor 4 are configured to be capable of performing bidirectional communication related to exchange of various signals and/or information and the like via a communication cable CC. FIG. 1 is a diagram showing a configuration of a main part of an endoscope system including a light source apparatus according to the first embodiment.

The endoscope 2 includes an elongated insertion section 6 insertable into the body cavity of the subject, an operation section 7 formed in a proximal end portion of the insertion section 6, a universal cable 8 provided to extend from the operation section 7, an optical connector 9 provided at an end portion of the universal cable 8, and an electric connector 10 provided at an end portion of an electric cable EC branching from the universal cable 8.

The operation section 7 has a shape for enabling a user such as a surgeon to grasp and operate the operation section 7. In the operation section 7, one or more scope switches (not shown in the figure) capable of giving an instruction corresponding to operation by the user to the video processor 4 is provided.

The optical connector 9 is configured to be detachably connected to a connector receiver (not shown in the figure) of the light source apparatus 3.

The electric connector 10 is configured to be detachably connected to a connector receiver (not shown in the figure) of the video processor 4.

The endoscope 2 includes a light guide 11 configured to transmit illumination light supplied from the light source apparatus 3 to which the optical connector 9 is connected, an illumination lens 12 disposed on an optical path of the illumination light emitted through the light guide 11, an objective lens 13 configured to form an optical image of the object illuminated by the illumination light emitted through the illumination lens 12, an image sensor 14 configured to pick up the optical image formed by the objective lens 13, and a memory 15 in which endoscopic information, which is information peculiar to each endoscope 2, is stored in advance.

The light guide 11 is inserted into insides of the insertion section 6, the operation section 7, and the universal cable 8. An incident end portion including a light incident surface of the light guide 11 is provided to extend from the optical connector 9. An emission end portion including a light emission surface of the light guide 11 is disposed near the light incident surface of the illumination lens 12.

The image sensor 14 includes a plurality of pixels (not shown in the figure) for photoelectrically converting the optical image formed by the objective lens 13 and a primary color filter (not shown in the figure) of a Bayer array provided on an image pickup surface on which the plurality of pixels are arrayed in a two-dimensional shape. The image sensor 14 is configured to photoelectrically convert the optical image formed by the objective lens 13 to generate an image pickup signal and output the generated image pickup signal to the video processor 4 to which the electric connector 10 is connected.

The video processor 4 includes one or more integrated circuits such as a control circuit and an image processing circuit. The video processor 4 is configured to be capable of reading, when the electric connector 10 is connected, the endoscopic information stored in the memory 15 and performing operation corresponding to the read endoscopic information. The video processor 4 is configured to generate, on the basis of a comparison result obtained by comparing brightness of an observation image obtained according to the image pickup signal outputted from the endoscope 2 and a brightness target value set in advance for each of a plurality of observation modes, a light amount adjustment signal for adjusting a light amount of the illumination light supplied from the light source apparatus 3 to the endoscope 2 and output the generated light amount adjustment signal to the light source apparatus 3.

The light source apparatus 3 includes a white light source 21 configured to emit white light, a lens 21a configured to collect the white light emitted from the white light source 21 and emit the white light, a white light source 22 configured to emit white light, a lens 22a configured to collect and emit the white light emitted from the white light source 22, a dichroic mirror 23, a lens 24, an operation panel 25, a light-source driving section 26, and a control section 27.

Figure 2:
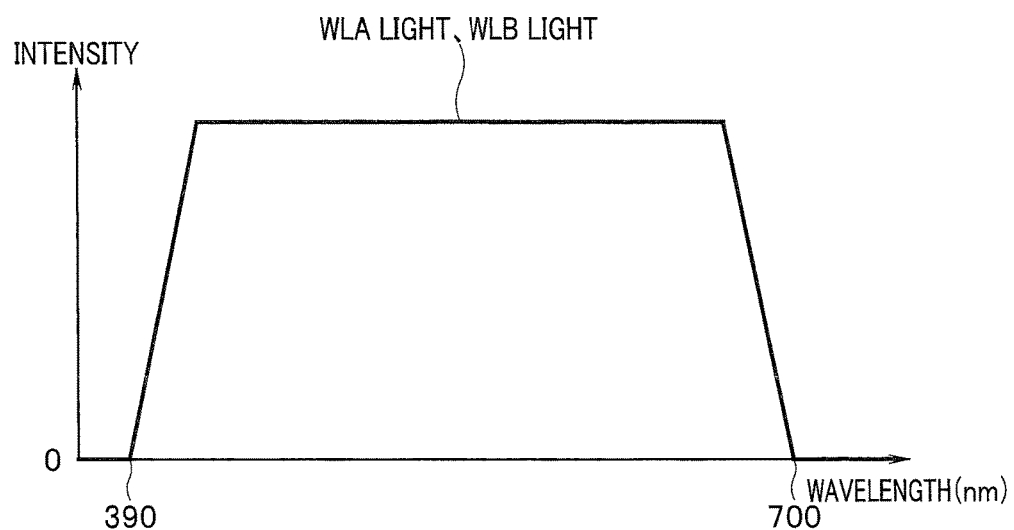
FIG. 2 is a diagram showing an example of a spectral distribution of white light emitted from a white light source provided in the light source apparatus according to the first embodiment.

The white light source 21 includes, for example, a Xenon lamp and is configured to emit light according to a light source driving signal supplied from the light-source driving section 26. The white light source 21 has a continuous spectral distribution shown in FIG. 2 in, for example, a wavelength band of 390 nm to 700 nm and is configured to generate WLA light, which is white light including wavelength bands of NBA light and NGA light explained below. FIG. 2 is a diagram showing an example of a spectral distribution of white light emitted from a white light source provided in the light source apparatus according to the first embodiment.

The white light source 22 includes, for example, a Xenon lamp and is configured to emit light according to the light source driving signal supplied from the light-source driving section 26. The white light source 22 has a continuous spectral distribution same as the spectral distribution of the WLA light shown in FIG. 2 in, for example, the wavelength band of 390 nm to 700 nm and is configured to generate WLB light, which is white light including the wavelength bands of the NBA light and the NGA light explained below.

That is, in the present embodiment, the spectral distribution of the WLA light and the spectral distribution of the WLB light are the same.

The dichroic mirror 23 has an optical characteristic for selectively reflecting, to the connector receiver side, a part of the WLA light emitted through the lens 21*a* and selectively transmitting, to the connector receiver side, a part of the WLB light emitted through the lens 22*a*.

Figure 3:
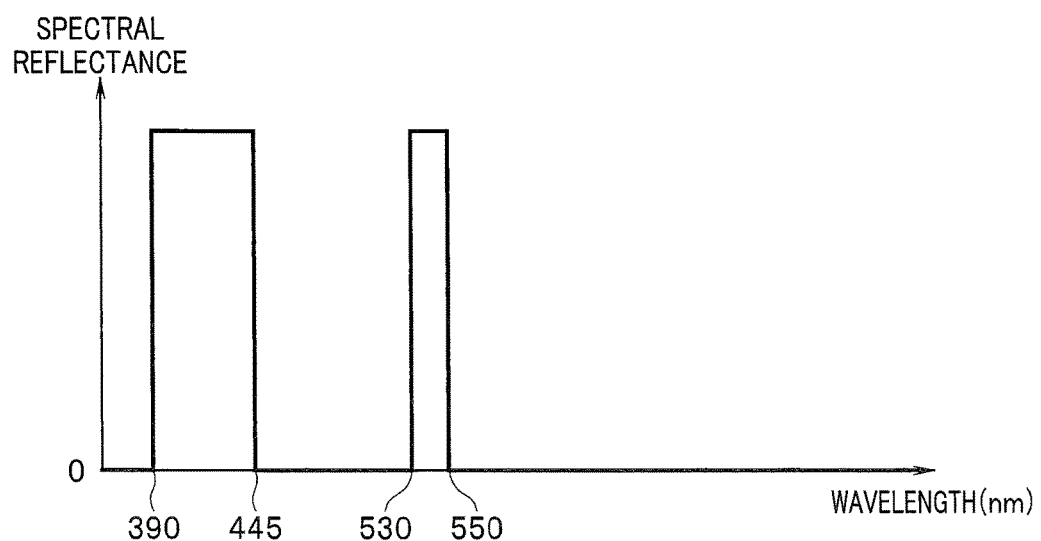
FIG. 3 is a diagram showing an example of a spectral reflection characteristic of a dichroic mirror provided in the light source apparatus according to the first embodiment.

More specifically, the dichroic mirror 23 has, for example, as shown in FIG. 3, a spectral reflection characteristic for selectively reflecting, to the connector receiver side, NBA light, which is light in a wavelength band of 390 nm to 445 nm, and NGA light, which is light in a wavelength band of 530 nm to 550 nm, in the WLA light emitted through the lens 21*a*. FIG. 3 is a diagram showing an example of a spectral reflection characteristic of a dichroic mirror provided in the light source apparatus according to the first embodiment.

The dichroic mirror 23 has a spectral transmission characteristic for selectively transmitting, to the connector receiver side, LOA light, which is the NGA light and light in a wavelength band other than that of the NBA light, in the WLB light emitted through the lens 22*a*.

That is, the dichroic mirror 23 has an optical characteristic in which a relational expression TX+RX=100% holds between spectral transmittance TX in a predetermined wavelength included in a wavelength band of the WLA light or the WLB light and spectral reflectance RX in the predetermined wavelength. The dichroic mirror 23 is configured as an optical member configured to extract NBA light and NGA light from the WLA light, extract LOA light from the WLB light, and mix and output the NBA light, the NGA light, and the LOA light.

The lens 24 is configured to collect the respective lights emitted through the dichroic mirror 23 and emit the lights to the light incident surface of the light guide 11 disposed near the connector receiver according to connection of the optical connector 9.

The operation panel 25 includes user interfaces such as a power supply switch (not shown in the figure) for enabling operations related to switching of ON/OFF of a power supply and an observation mode selection switch (not shown in the figure) for enabling operations for selecting a desired observation mode out of a plurality of observation modes.

The light-source driving section 26 is configured to generate and output, according to control by the control section 27, light source driving signals for respectively driving the white light sources 21 and 22.

The control section 27 is configured to perform, according to operation performed in the observation mode selection switch of the operation panel 25, on the light-source driving section 26, control for individually setting light emission states of the white light sources 21 and 22. The control section 27 is configured to perform, on the basis of a light amount adjustment signal outputted from the video processor 4 via the communication cable CC, on the light-source driving section 26, control for respectively adjusting light amounts of the WLA light and the WLB light.

Operation and the like of the endoscope system 1 including the light source apparatus 3 according to the present embodiment are explained.

For example, after connecting the respective sections of the endoscope system 1 and turning on the power supply, the user such as the surgeon performs operation for selecting the white light observation mode in the observation mode selection switch of the operation panel 25.

When detecting that operation for selecting the white light observation mode is performed in the observation mode selection switch of the operation panel 25, the control section 27 performs, on the light-source driving section 26, control for causing both of the white light sources 21 and 22 to simultaneously emit lights.

Figure 4:
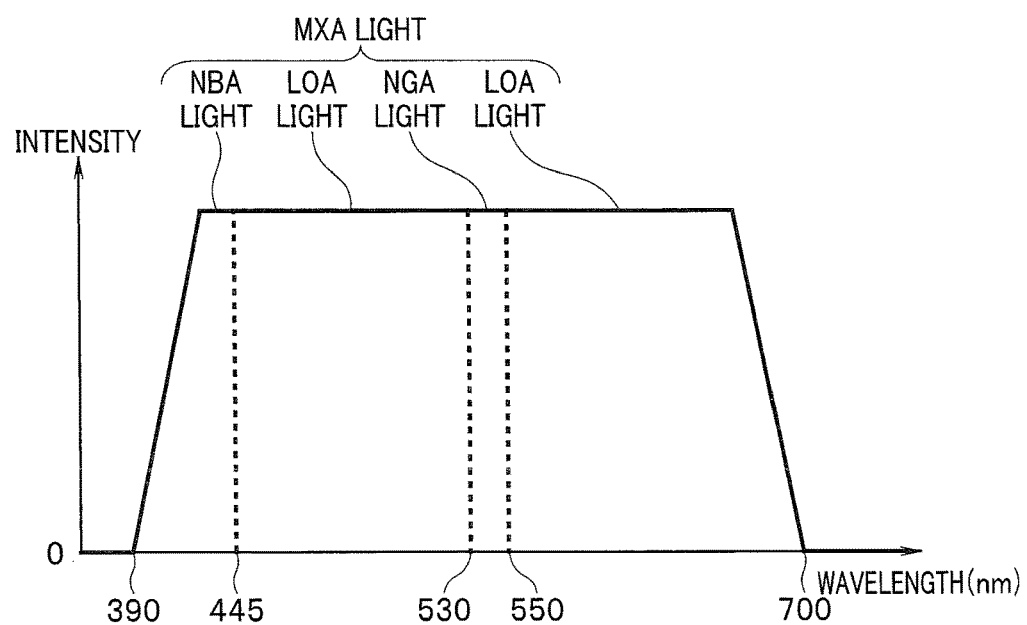
FIG. 4 is a diagram showing an example of a spectral distribution of illumination light emitted from the light source apparatus according to the first embodiment when a white light observation mode is selected.

According to the control by the control section 27 explained above, the WLA light emitted from the white light source 21 is separated into NBA light and NGA light according to the spectral reflection characteristic of the dichroic mirror 23, the WLB light emitted from the white light source 22 is separated into LOA light according to the spectral transmission characteristic of the dichroic mirror 23, and MXA light, which is mixed light obtained by mixing the NBA light, the NGA light, and the LOA light, is supplied to the endoscope 2 as illumination light. That is, the MXA light, which is white light, supplied from the light source apparatus 3 as the illumination light of the white light observation mode has a spectral distribution illustrated in FIG. 4. FIG. 4 is a diagram showing an example of a spectral distribution of illumination light emitted from the light source apparatus according to the first embodiment when the white light observation mode is selected.

According to the control by the control section 27 explained above, an optical image of the object illuminated by the MXA light is picked up by the image sensor 14 and a white light observation image generated according to an image pickup signal outputted from the image sensor 14 is displayed on the monitor 5 on a frame-by-frame basis. That is, in the white light observation mode, for example, a white light observation image having visibility substantially the same as visibility of the object viewed by naked eyes is displayed on the monitor 5.

On the other hand, for example, after disposing the insertion section 6 in a position where a desired biological tissue present in the body cavity of the subject can be visually recognized by the white light observation image, the user performs, in the observation mode selection switch of the operation panel 25, operation for selecting a narrow band light observation mode included in one kind of the special light observation mode.

When detecting that the operation for selecting the narrow band light observation mode is performed in the observation mode selection switch of the operation panel 25, the control section 27 performs, on the light-source driving section 26, control for causing only the white light source 21 to emit light.

Figure 5:
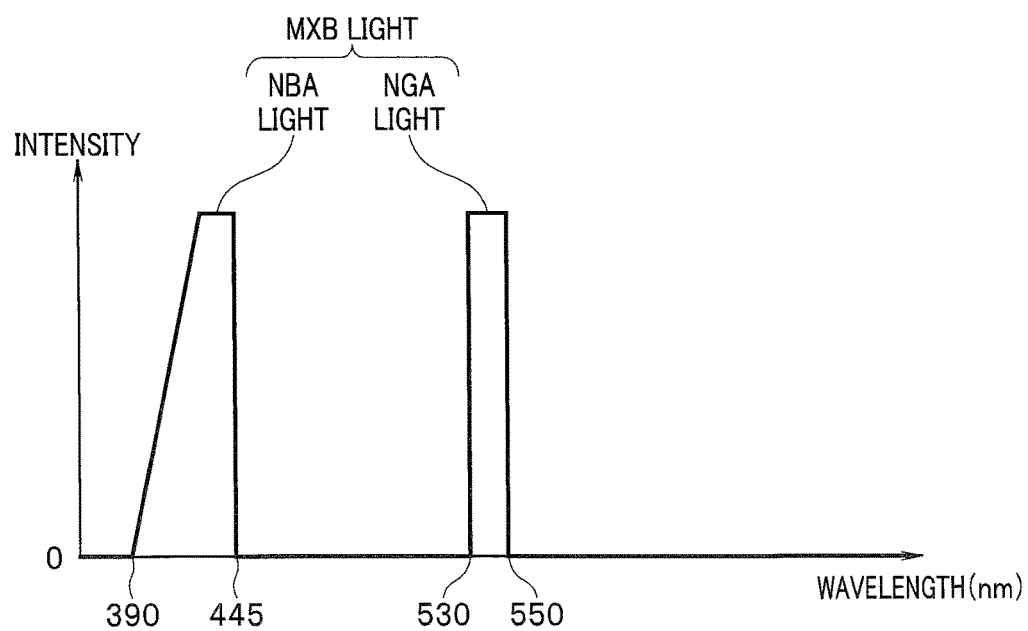
FIG. 5 is a diagram showing an example of a spectral distribution of illumination light emitted from the light source apparatus according to the first embodiment when a narrow band light observation mode is selected.

According to the control by the control section 27 explained above, the WLA light emitted from the white light source 21 is separated into NBA light and NGA light according to the spectral reflection characteristic of the dichroic mirror 23 and MXB light, which is mixed light obtained by mixing the NBA light and the NGA light, is supplied to the endoscope 2 as illumination light. That is, the MXB light, which is special light supplied from the light source apparatus 3 as the illumination light of the narrow band light observation mode, is light narrower in a band than the MXA light and has a spectral distribution illustrated in FIG. 5. FIG. 5 is a diagram showing an example of a spectral distribution of illumination light emitted from the light source apparatus according to the first embodiment when the narrow band light observation mode is selected.

According to the control by the control section 27 explained above, an optical image of a desired biological tissue illuminated by the MXB light is picked up by the image sensor 14 and a narrow band light observation image generated according to an image pickup signal outputted from the image sensor 14 is displayed on the monitor 5 on a frame-by-frame basis. That is, in the narrow band light observation mode, for example, a narrow band light observation image in which visibilities of a capillary and a mucous membrane structure present in a surface layer of the desired biological tissue and a blood vessel present in an intermediate layer of the desired biological tissue are respectively improved compared with the visibilities in the white light observation mode is displayed on the monitor 5.

Note that, according to the present embodiment, as long as the MXA light is supplied as the illumination light for obtaining the white light observation image and the MXB light is supplied as the illumination light for obtaining the narrow band light observation image, the dichroic mirror 23 may be configured as an optical member configured to extract NBA light and NGA light from the WLB light, extract LOA light from the WLA light, and mix and emit the NBA light, the NGA light, and the LOA light. More specifically, for example, by interchanging the spectral reflection characteristic and the spectral transmission characteristic of the dichroic mirror 23 each other, the NBA light and the NGA light of the WLB light emitted through the lens 22a may be selectively transmitted to the connector receiver side and the LOA light of the WLA light emitted through the lens 21a may be selectively reflected to the connector receiver side. In such a configuration, when the white light observation mode is selected, control for causing the white light sources 21 and 22 to simultaneously emit lights only has to be performed by the control section 27. When the narrow band light observation mode is selected, as control for setting a light amount ratio of the white light source 21 and the white light source 22 to a ratio different from the light amount ratio in the white light observation mode, for example, control for causing only the white light source 22 to emit light only has to be performed by the control section 27. For example, the dichroic mirror 23 may have a spectral reflection characteristic for selectively reflecting one light of the NBA light and the NGA light included in the WLB light to the connector receiver side and have a spectral transmission characteristic for selectively transmitting light in a wavelength band other than the wavelength band of the one light in the WLB light to the connector receiver side.

In the present embodiment, the white light sources 21 and 22 are not limited to white light sources including Xenon lamps and may include solid-state light sources such as LEDs or LDs (laser diodes) that emit white lights.

The present embodiment is not limited to be applied when spectral distributions of the WLA light and the WLB light are completely the same but is also applied when the spectral distributions of the WLA light and the WLB light are substantially the same.

By appropriately modifying the present embodiment, for example, either one of the white light source 21 and the white light source 22 may be set as light sources of three colors, that is, a red light source, a green light source, and a blue light source. The spectral reflection characteristic and the spectral transmission characteristic of the dichroic mirror 23 may be set such that the MXA light and the MXB light are generated according to spectral distributions of lights respectively emitted from the light sources of the three colors.

As explained above, with the light source apparatus 3 according to the present embodiment, with a simple configuration for switching the light emission states of the white light sources 21 and 22 according to the observation mode selected in the observation mode selection switch of the operation panel 25, it is possible to supply the MXA light to the endoscope 2 as the illumination light of the white light observation mode. It is possible to supply the MXB light to the endoscope 2 as the illumination light of the narrow band light observation mode. Therefore, with the light source apparatus 3 according to the present embodiment, it is possible to further simplify a configuration for performing the white light observation and the special light observation than in the past.

Second Embodiment

FIG. 6 to FIG. 15 relate to a second embodiment of the present invention.

Note that, in the present embodiment, detailed explanation concerning portions including components and the like same as the components and the like in the first embodiment is omitted. Portions including components and the like different from the components and the like in the first embodiment are mainly explained.

Figure 6:
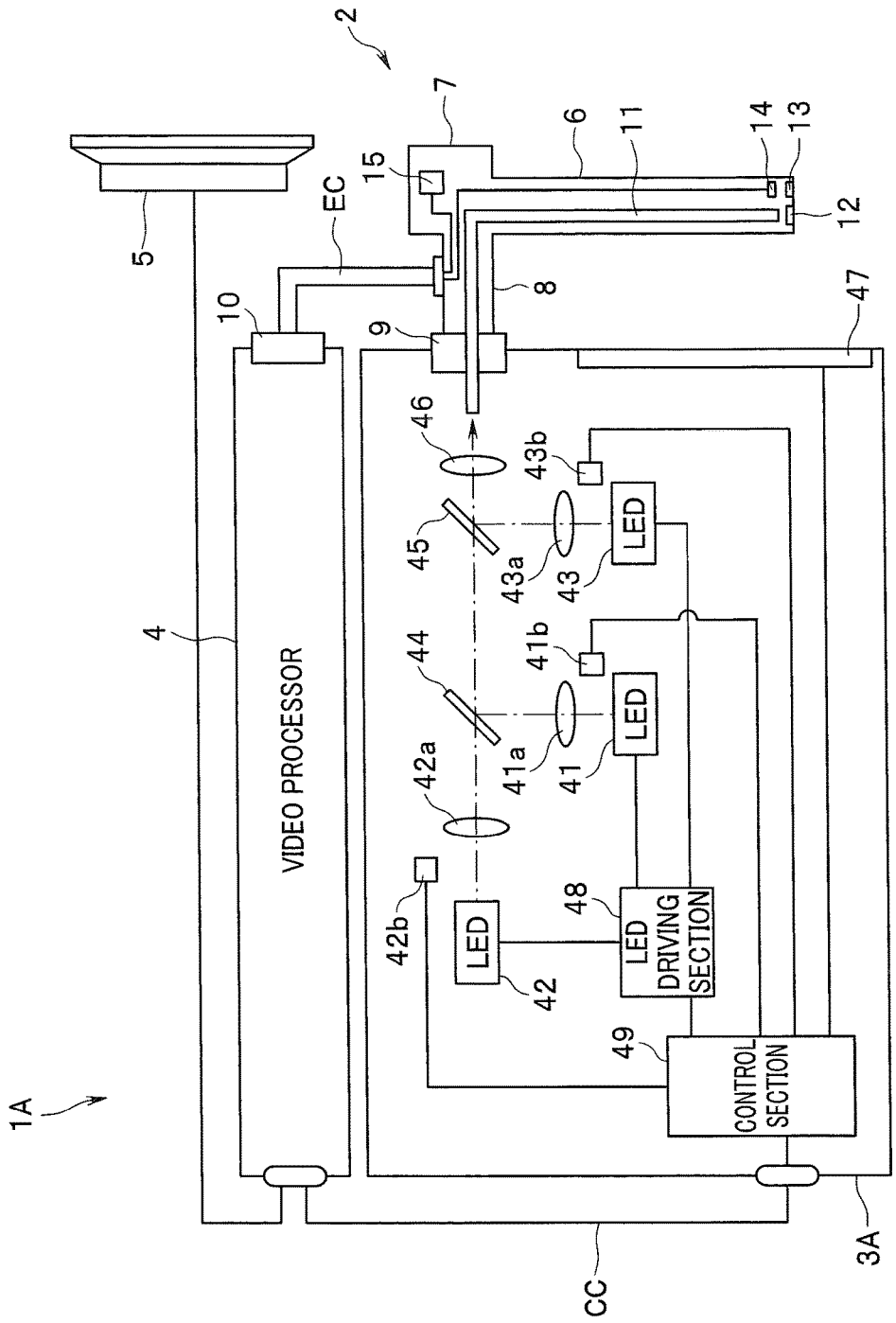
FIG. 6 is a diagram showing a configuration of a main part of an endoscope system including a light source apparatus according to a second embodiment.

An endoscope system 1A includes, as shown in FIG. 6, instead of the light source apparatus 3 in the endoscope system 1, a light source apparatus 3A configured to supply illumination light for illuminating an object to the endoscope 2. FIG. 6 is a diagram showing a configuration of a main part of an endoscope system including a light source apparatus according to the second embodiment.

The light source apparatus 3A includes an LED 41, which is a solid-state light source configured to emit white light, a lens 41a configured to collect and emit the white light emitted from the LED 41, and an optical sensor 41b disposed near the LED 41 and configured to detect a light amount of the white light emitted from the LED 41 and generate and output a light amount detection signal indicating the detected light amount.

Figure 7:
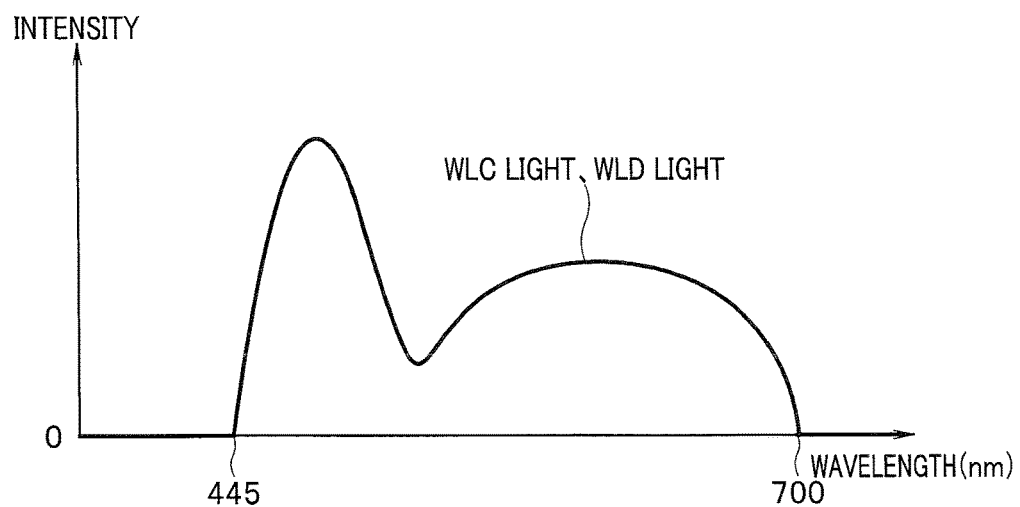
FIG. 7 is a diagram showing an example of a spectral distribution of light emitted from an LED provided in the light source apparatus according to the second embodiment.

The LED 41 is configured to emit light according to an LED driving signal supplied from the LED driving section 48. The LED 41 has a continuous spectral distribution shown in FIG. 7 in a wavelength band of 445 nm to 700 nm and is configured to generate WLC light, which is white light including a wavelength band of NGB light explained below. FIG. 7 is a diagram showing an example of a spectral distribution of light emitted from an LED provided in the light source apparatus according to the second embodiment.

The light source apparatus 3A includes an LED 42, which is a solid-state light source configured to emit white light, a lens 42a configured to collect and emit the white light emitted from the LED 42, and an optical sensor 42b disposed near the LED 42 and configured to detect a light amount of the white light emitted from the LED 42 and generate and output a light amount detection signal indicating the detected light amount.

The LED 42 is configured to emit light according to an LED driving signal supplied from the LED driving section 48. The LED 42 has a continuous spectral distribution same as the spectral distribution of the WLC light shown in FIG. 7 in the wavelength band of 445 nm to 700 nm and is configured to generate WLD light, which is white light including the wavelength band of NGB light explained below.

That is, in the present embodiment, the spectral distribution of the WLC light and the spectral distribution of the WLD light are the same.

The light source apparatus 3A includes an LED 43, which is a solid-state light source configured to emit light in a wavelength band of purple to blue, a lens 43a configured to collect and emit the light emitted from the LED 43, and an optical sensor 43b disposed near the LED 43 and configured to detect a light amount of the light emitted from the LED 43 and generate and output a light amount detection signal indicating the detected light amount.

Figure 8:
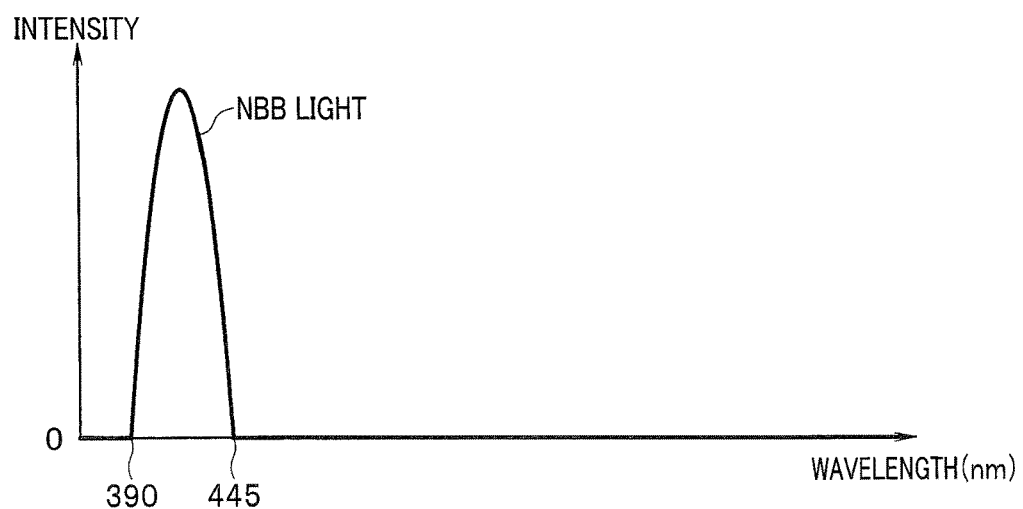
FIG. 8 is a diagram showing an example of a spectral distribution of light emitted from an LED provided in the light source apparatus according to the second embodiment.

The LED 43 is configured to emit light according to an LED driving signal supplied from the LED driving section 48. The LED 43 is configured to generate NBB light, which is narrow band light having a spectral distribution shown in FIG. 8 in, for example, a wavelength band of 390 nm to 445 nm. FIG. 8 is a diagram showing an example of a spectral distribution of light emitted from an LED provided in the light source apparatus according to the second embodiment.

The light source apparatus 3A includes dichroic mirrors 44 and 45, a lens 46, an operation panel 47, an LED driving section 48, and a control section 49.

The dichroic mirror 44 has an optical characteristic for selectively reflecting, to the connector receiver side, a part of the WLC light emitted through the lens 41a and selectively transmitting, to the connector receiver side, a part of the WLD light emitted through the lens 42a.

Figure 9:
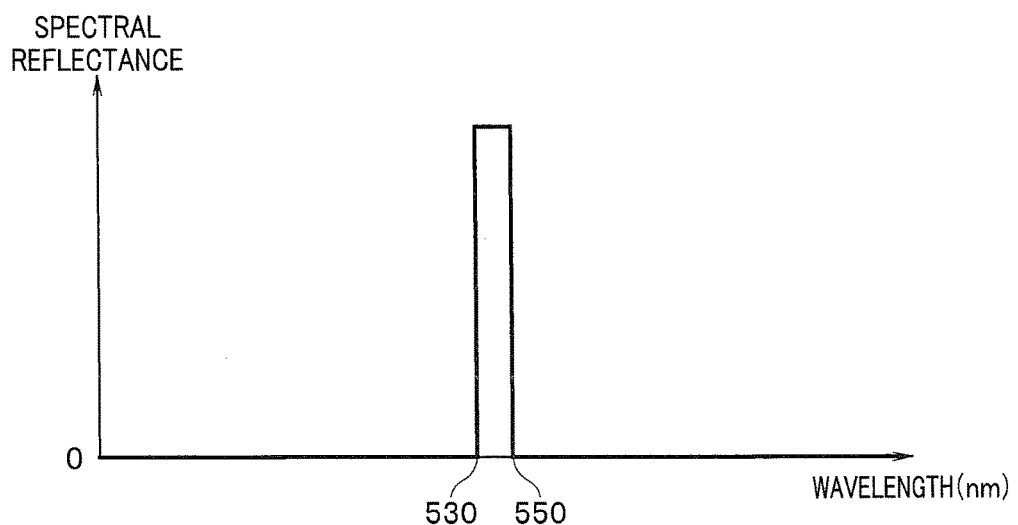
FIG. 9 is a diagram showing an example of a spectral reflection characteristic of a dichroic mirror provided in the light source apparatus according to the second embodiment.

More specifically, the dichroic mirror 44 has, for example, as shown in FIG. 9, a spectral reflection characteristic for selectively reflecting, to the connector receiver side, NGB light, which is light in a wavelength band of 530 nm to 550 nm, in the WLC light emitted through the lens 41a. FIG. 9 is a diagram showing an example of a spectral reflection characteristic of a dichroic mirror provided in the light source apparatus according to the second embodiment.

The dichroic mirror 44 has a spectral transmission characteristic for selectively transmitting, to the connector receiver side, LOB light, which is light in a wavelength band other than that of the NGB light, in the WLD light emitted through the lens 42a.

That is, the dichroic mirror 44 has an optical characteristic in which a relational expression of TY+RY=100% holds between spectral transmittance TY in a predetermined wavelength included in the wavelength band of the WLC light or the WLD light and spectral reflectance RY in the predetermined wavelength. The dichroic mirror 44 is configured as an optical member configured to extract NGB light from the WLC light, extract LOB light from the WLD light, and mix and emit the NGB light and the LOB light.

Figure 10:
FIG. 10 is a diagram showing an example of a spectral reflection characteristic of a dichroic mirror provided in the light source apparatus according to the second embodiment.

The dichroic mirror 45 has, for example, as shown in FIG. 10, a spectral reflection characteristic for reflecting, to the connector receiver side, NBB light emitted through the lens 43a. FIG. 10 is a diagram showing an example of a spectral reflection characteristic of a dichroic mirror provided in the light source apparatus according to the second embodiment.

The dichroic mirror 45 has a spectral transmission characteristic for transmitting, to the connector receiver side, NGB light and LOB light emitted through the dichroic mirror 44.

The lens 46 is configured to collect the respective lights emitted through the dichroic mirror 45 and emit the lights to a light incident surface of the light guide 11 disposed near the connector receiver according to connection of the optical connector 9.

The operation panel 47 includes user interfaces such as a power supply switch (not shown in the figure) for enabling a user to perform operation related to switching of ON/OFF of a power supply and an observation mode selection switch (not shown in the figure) for enabling operations for selecting a desired observation mode out of a plurality of observation modes.

The LED driving section 48 is configured to generate and output, according to control by the control section 49, LED driving signals for respectively driving the LEDs 41 to 43.

The control section 49 is configured to perform, according to operation performed in the observation mode selection switch of the operation panel 47, on the LED driving section 48, control for individually setting light emission states of the LEDs 41 to 43. The control section 49 is configured to perform, on the basis of a light amount adjustment signal outputted from the video processor 4 via the communication cable CC and light amount detection signals outputted from the optical sensors 41b to 43b, on the LED driving section 48, control for respectively adjusting light amounts of the WLC light, the WLD light, and the NBB light according to the observation mode selected in the observation mode selection switch of the operation panel 47.

Operation and the like of the endoscope system 1A including the light source apparatus 3A according to the present embodiment are explained.

For example, after connecting the respective sections of the endoscope system 1A and turning on the power supply, the user such as a surgeon performs operation for selecting a white light observation mode in the observation mode selection switch of the operation panel 47.

When detecting that the operation for selecting the white light observation mode is performed in the observation mode selection switch of the operation panel 47, the control section 49 performs, on the LED driving section 48, control for causing three LEDs of the LEDs 41 to 43 to simultaneously emit lights.

Figure 11:
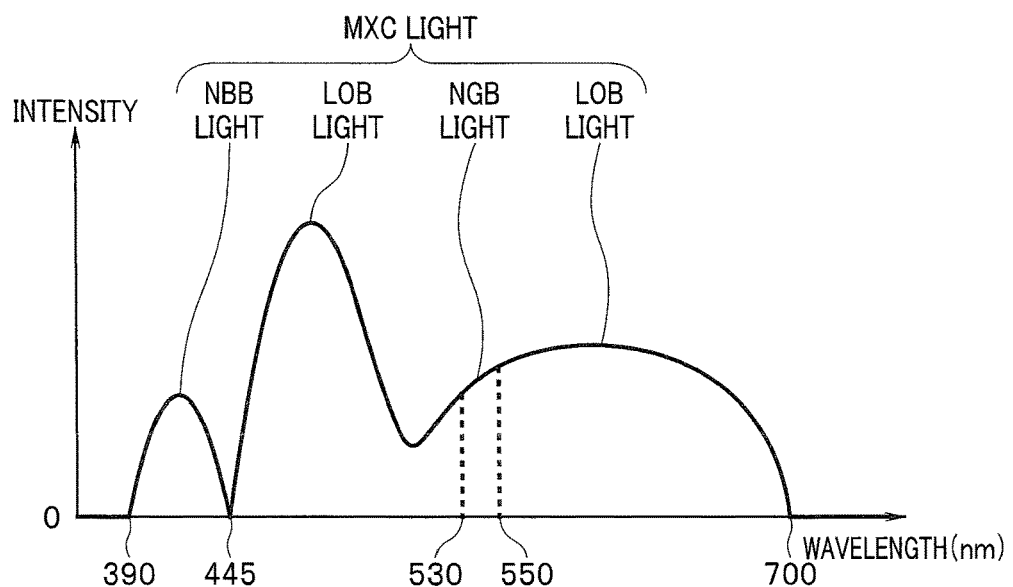
FIG. 11 is a diagram showing an example of a spectral distribution of illumination light emitted from the light source apparatus according to the second embodiment when the white light observation mode is selected.

According to the control by the control section 49 explained above, the WLC light emitted from the LED 41 is separated into NGB light according to the spectral reflection characteristic of the dichroic mirror 44, the WLD light emitted from the LED 42 is separated into LOB light according to the spectral transmission characteristic of the dichroic mirror 44, and MXC light, which is mixed light obtained by mixing, with the dichroic mirror 45, the NGB light, the LOB light, and NBB light emitted from the LED 43, is supplied to the endoscope 2 as illumination light. That is, the MXC light, which is white light, supplied from the light source apparatus 3A as the illumination light of the white light observation mode has a spectral distribution illustrated in FIG. 11. FIG. 11 is a diagram showing an example of a spectral distribution of illumination light emitted from the light source apparatus according to the second embodiment when the white light observation mode is selected. Note that it is assumed that a spectral distribution of the NBB light shown in FIG. 11 indicates an example of a spectral distribution at a time when light amount adjustment is performed to obtain a light amount suitable for observation by a white light observation image.

According to the control by the control section 49 explained above, an optical image of the object illuminated by the MXC light is picked up by the image sensor 14 and a white light observation image generated according to an image pickup signal outputted from the image sensor 14 is displayed on the monitor 5 on a frame-by-frame basis.

The control section 49 performs, on the basis of a light amount adjustment signal outputted from the video processor 4 via the communication cable CC and light amount detection signals outputted from the optical sensors 41b to 43b, on the LED driving section 48, control for respectively adjusting light amounts of the WLC light, the WLD light, and the NBB light to light amounts suitable for the observation by the white light observation image.

More specifically, the control section 49 performs, for example, on the basis of a light amount adjustment signal outputted from the video processor 4 for each one frame period TFA equivalent to a display period of the white light observation image for one frame and a light amount detection signal outputted from the optical sensor 41b, on the LED driving section 48, control for setting a light amount of the WLC light. The control section 49 performs, for example, on the basis of light amount detection signals outputted from the optical sensors 41b to 43b, control for respectively setting a light amount ratio RA of a light amount of WLD light to the light amount of the WLC light set as explained above and a light amount ratio RB of a light amount of NBB light to the light amount of the WLC light set as explained above to obtain a color balance suitable for the observation by the white light observation image. More specifically, the control section 49 sets the light amount ratio RA such that a spectral distribution of mixed light obtained by mixing the NGB light and the LOB light coincides with a spectral distribution of either one of the WLC light and the WLD light.

The LED driving section 48 generates pulse-like LED driving signals having a pulse width and a pulse height corresponding to the control by the control section 49 and outputs the generated LED driving signals respectively to the LEDs 41 to 43.

Figure 12:
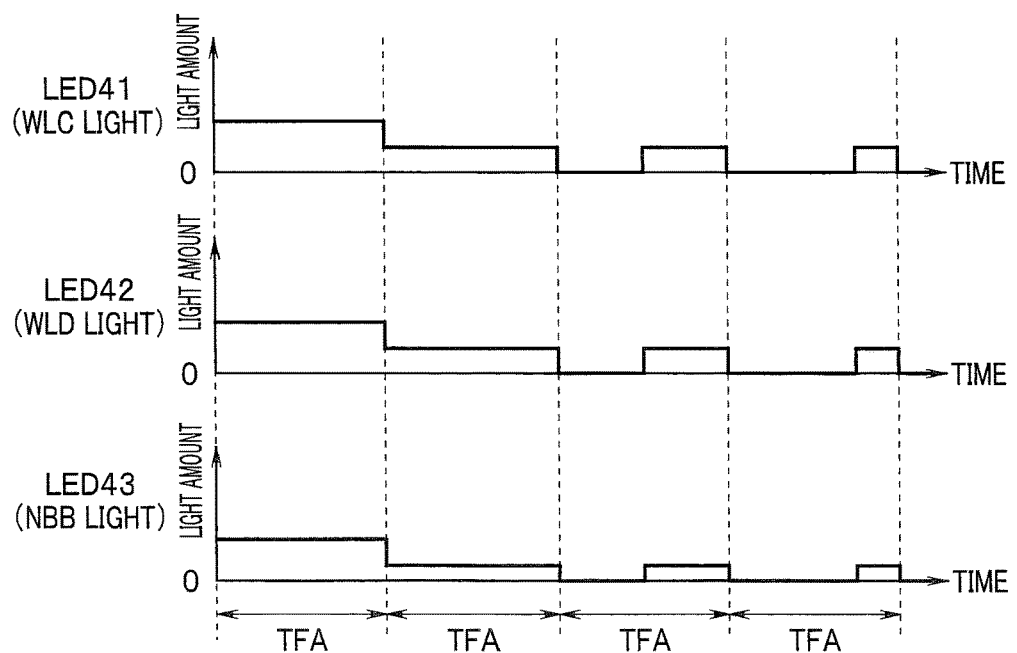
FIG. 12 is a diagram for explaining an example of light amount adjustment performed in the light source apparatus according to the second embodiment when the white light observation mode is selected.

With the operations of the LED driving section 48 and the control section 49 explained above, for example, when a comparison result indicating that brightness of a white light observation image generated according to an image pickup signal outputted from the endoscope 2 exceeds a brightness target value WBT of the white light observation mode is continuously obtained, light amount adjustment for gradually reducing the light amounts of the WLC light, the WLD light, and the NBB light while respectively maintaining the light amount ratios RA and RB to obtain a color balance suitable for the observation by the white light observation image is performed for each one frame period TFA (see FIG. 12). FIG. 12 is a diagram for explaining an example of light amount adjustment performed in the light source apparatus according to the second embodiment when the white light observation mode is selected.

On the other hand, for example, after disposing the insertion section 6 in a position where a desired biological tissue present in the body cavity of the subject can be visually recognized by the white light observation image, the user performs, in the observation mode selection switch of the operation panel 47, operation for selecting a narrow band light observation mode included in one kind of the special light observation mode.

When detecting that the operation for selecting the narrow band light observation mode is performed in the observation mode selection switch of the operation panel 47, the control section 49 performs, on the LED driving section 48, control for extinguishing the LED 42 while causing the LEDs 41 and 43 to simultaneously emit lights.

Figure 13:
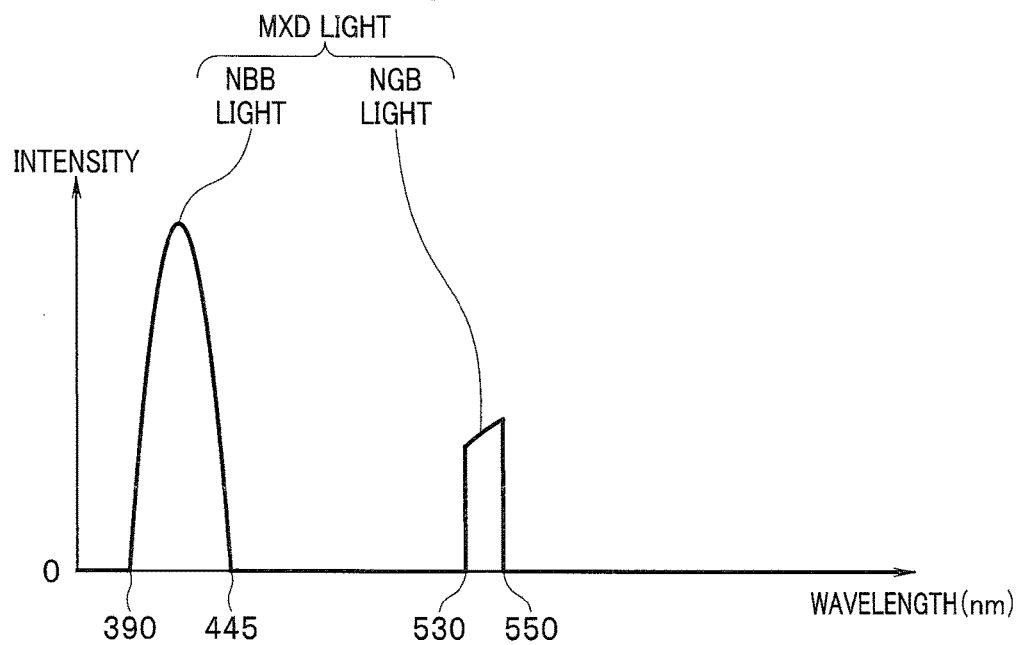
FIG. 13 is a diagram showing an example of a spectral distribution of illumination light emitted from the light source apparatus according to the second embodiment when the narrow band light observation mode is selected.

According to the control by the control section 49 explained above, the WLC light emitted from the LED 41 is separated into NGB light according to the spectral reflection characteristic of the dichroic mirror 44 and MXD light, which is mixed light obtained by mixing, with the dichroic mirror 45, the NGB light and NBB light emitted from the LED 43, is supplied to the endoscope 2 as illumination light. That is, the MXD light, which is special light supplied from the light source apparatus 3A as the illumination light of the narrow band light observation mode, is light narrower in a band than the MXC light and has a spectral distribution illustrated in FIG. 13. FIG. 13 is a diagram showing an example of a spectral distribution of illumination light emitted from the light source apparatus according to the second embodiment when the narrow band light observation mode is selected.

According to the control by the control section 49 explained above, an optical image of the object illuminated by the MXD light is picked up by the image sensor 14 and a narrow band light observation image generated according to an image pickup signal outputted from the image sensor 14 is displayed on the monitor 5 on a frame-by-frame basis.

The control section 49 performs, on the basis of a light amount adjustment signal outputted from the video processor 4 via the communication cable CC and light amount detection signals outputted from the optical sensors 41b and 43b, on the LED driving section 48, control for respectively adjusting light amounts of the WLC light and the NBB light to light amounts suitable for the observation by the narrow band light observation image.

More specifically, the control section 49 performs, for example, on the basis of a light amount adjustment signal outputted from the video processor 4 for each one frame period TFB equivalent to a display period of the narrow band light observation image for one frame and a light amount detection signal outputted from the optical sensor 41b, on the LED driving section 48, control for setting a light amount of the WLC light. The control section 49 performs, for example, on the basis of light amount detection signals outputted from the optical sensors 41b to 43b, control for setting a light amount ratio RC of the light amount of NBB light to the light amount of the WLC light set as explained above to obtain a color balance suitable for the observation by the narrow band light observation image.

The LED driving section 48 generates pulse-like LED driving signals having a pulse width and a pulse height corresponding to the control by the control section 49 and outputs the generated LED driving signals respectively to the LEDs 41 and 43.

Figure 14:
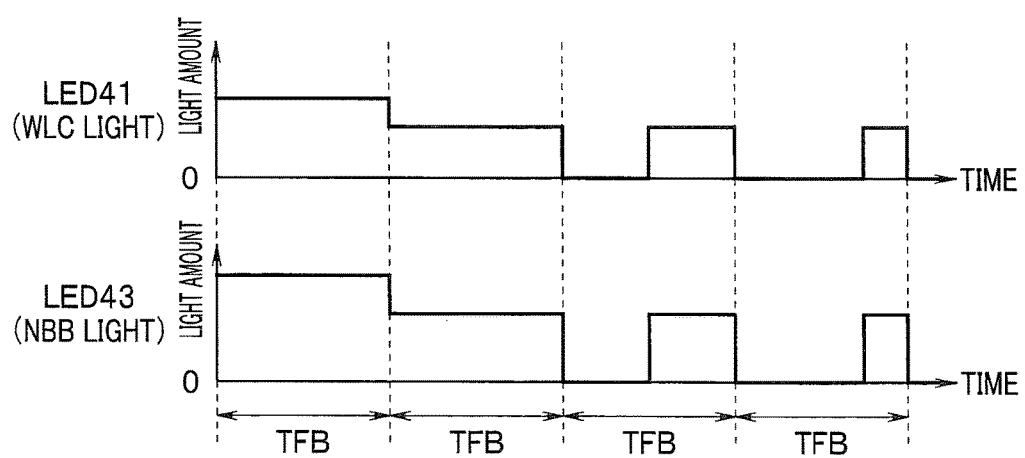
FIG. 14 is a diagram for explaining an example of light amount adjustment performed in the light source apparatus according to the second embodiment when the narrow band light observation mode is selected.

With the operations of the LED driving section 48 and the control section 49 explained above, for example, when a comparison result indicating that brightness of a narrow band light observation image generated according to an image pickup signal outputted from the endoscope 2 exceeds a brightness target value NBT of the narrow band light observation mode is continuously obtained, light amount adjustment for gradually reducing the light amounts of the WLC light and the NBB light while maintaining the light amount ratio RC to obtain a color balance suitable for the observation by the narrow band light observation image is performed for each one frame period TFB (see FIG. 14). FIG. 14 is a diagram for explaining an example of light amount adjustment performed in the light source apparatus according to the second embodiment when the narrow band light observation mode is selected.

On the other hand, for example, after disposing the insertion section 6 in a position where a desired biological tissue present in the body cavity of the subject can be visually recognized by the white light observation image, the user performs, in the observation mode selection switch of the operation panel 47, operation for selecting a simultaneous observation mode, which is a mode for simultaneously displaying the white light observation image and the narrow band light observation image.

When detecting that the operation for selecting the simultaneous observation mode is performed in the observation mode selection switch of the operation panel 47, the control section 49 performs, on the LED driving section 48, control for causing the LED driving section 48 to alternately repeat a light emission period IPA for causing the three LEDs of the LEDs 41 to 43 to simultaneously emit lights and a light emission period IPB for extinguishing the LED 42 while causing the LEDs 41 and 43 to simultaneously emit lights.

According to the control by the control section 49 explained above, the MXC light is supplied to the endoscope 2 as illumination light in the light emission period IPA and the MXD light is supplied to the endoscope 2 as illumination light in the light emission period IPB. That is, in the simultaneous observation mode according to the present embodiment, the object is irradiated with the MXC light and the MXD light in a time-division manner.

According to the control by the control section 49 explained above, a white light observation image for one field is generated according to the irradiation of the object with the MXC light, a narrow band light observation image for one field is generated according to the irradiation of the MXD light on the object, and a simultaneous observation image generated by joining the white light observation image and the narrow band light observation image for each one field is displayed on the monitor 5 on a frame-by-frame basis.

The control section 49 performs, on the basis of a light amount adjustment signal outputted from the video processor 4 every time a white light observation image for one field is generated and light amount detection signals outputted from the optical sensors 41b to 43b, on the LED driving section 48, control for causing the LED driving section 48 to perform, in the light emission period IPA, the light amount adjustment corresponding to the white light observation mode explained above. The control section 49 performs, on the basis of a light amount adjustment signal outputted from the video processor 4 every time a narrow band light observation image for one field is generated and light amount detection signals outputted from the optical sensors 41b and 43b, on the LED driving section 48, control for causing the LED driving section 48 to perform, in the light emission period IPB, the light amount adjustment corresponding to the narrow band light observation mode explained above.

In the light emission period IPA, the LED driving section 48 generates pulse-like LED driving signals having a pulse width and a pulse height corresponding to the control by the control section 49 and outputs the generated LED driving signals respectively to the LEDs 41 to 43. In the light emission period IPB, the LED driving section 48 generates pulse-like LED driving signals having a pulse width and a pulse height corresponding to the control by the control section 49 and outputs the generated LED driving signals respectively to the LEDs 41 and 43.

Figure 15:
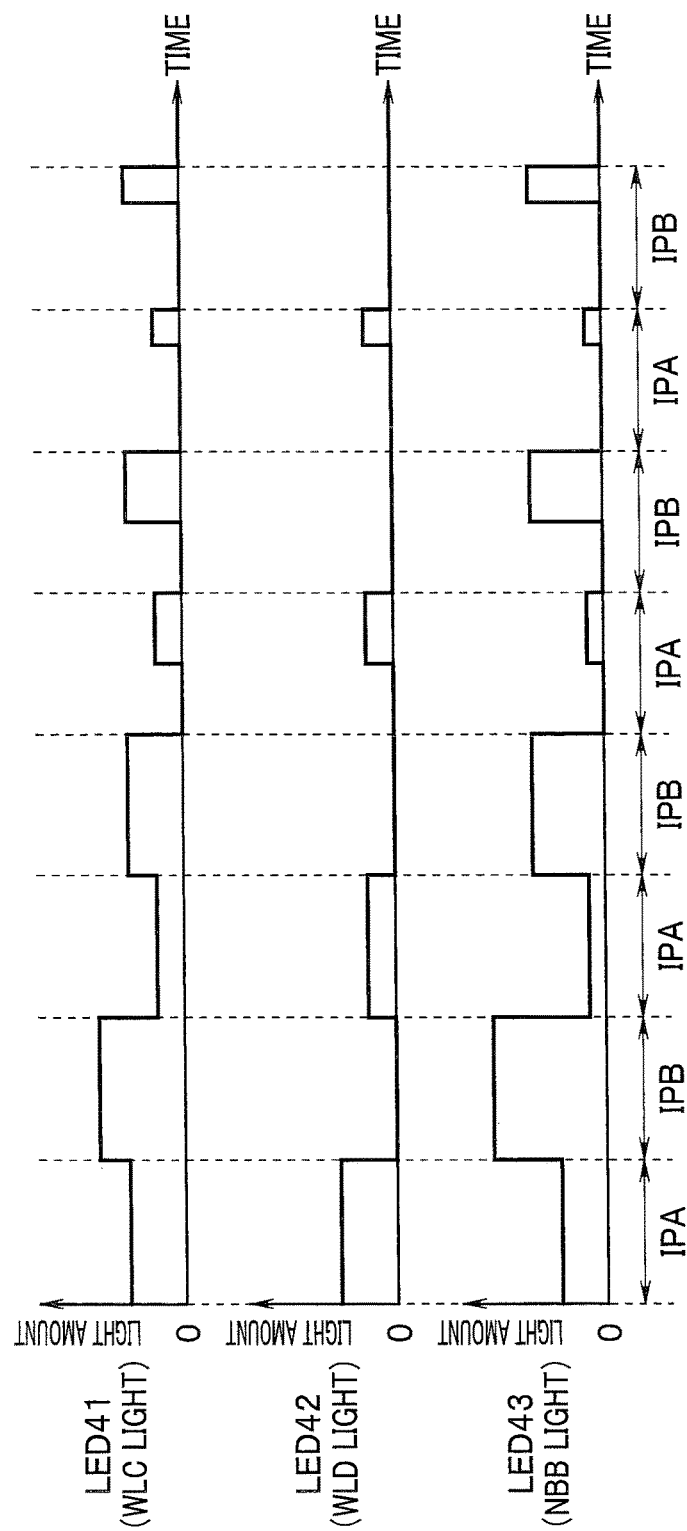
FIG. 15 is a diagram for explaining an example of light amount adjustment performed in the light source apparatus according to the second embodiment when a simultaneous observation mode is selected.

With the operations of the LED driving section 48 and the control section 49 explained above, for example, when a comparison result indicating that brightness of a white light observation image for one field generated according to an image pickup signal outputted from the endoscope 2 exceeds the brightness target value WBT is continuously obtained, light amount adjustment for gradually reducing the light amounts of the WLC light, the WLD light, and the NBB light while maintaining the light amount ratios RA and RB to obtain a color balance suitable for the observation by the white light observation image is performed for each light emission period IPA (see FIG. 15). With the operations of the LED driving section 48 and the control section 49 explained above, for example, when a comparison result indicating that brightness of a narrow band light observation image for one field generated according to an image pickup signal outputted from the endoscope 2 exceeds the brightness target value NBT is continuously obtained, light amount adjustment for gradually reducing the light amounts of the WLC light and the NBB light while maintaining the light amount ratio RC to obtain a color balance suitable for the observation by the narrow band light observation image is performed for each light emission period IPB (see FIG. 15). FIG. 15 is a diagram for explaining an example of light amount adjustment performed in the light source apparatus according to the second embodiment when the simultaneous observation mode is selected.

Note that, according to the present embodiment, as long as the MXC light is supplied as the illumination light for obtaining the white light observation image and the MXD light is supplied as the illumination light for obtaining the narrow band light observation image, the dichroic mirror 44 may be configured as an optical member configured to extract NGB light from the WLD light, extract LOB light from the WLC light, and mix and emit the NGB light and the LOB light. More specifically, for example, by interchanging the spectral reflection characteristic and the spectral transmission characteristic of the dichroic mirror 44 each other, the NGB light in the WLD light emitted through the lens 42a may be selectively transmitted to the connector receiver side and the LOB light in the WLC light emitted through the lens 41a may be selectively reflected to the connector receiver side. In such a configuration, when the white light observation mode is selected, control for causing the LEDs 41 to 43 to simultaneously emit lights only has to be performed by the control section 49. When the narrow band light observation mode is selected, control for causing the LEDs 42 and 43 to simultaneously emit lights only has to be performed by the control section 49.

The present embodiment is not limited to be applied when spectral distributions of the WLC light and the WLD light are completely the same and is also applied when the spectral distributions of the WLC light and the WLD light are substantially the same.

As explained above, with the light source apparatus 3A according to the present embodiment, with a simple configuration for switching the light emission states of the LEDs 41 to 43 according to the observation mode selected in the observation mode selection switch of the operation panel 47, it is possible to supply the MXC light to the endoscope 2 as the illumination light of the white light observation mode. It is possible to supply the MXD light to the endoscope 2 as the illumination light of the narrow band light observation mode. Therefore, with the light source apparatus 3A according to the present embodiment, it is possible to further simplify a configuration for performing the white light observation and the special light observation than in the past.

With the light source apparatus 3A according to the present embodiment, it is possible to irradiate the object with the MXC light and the MXD light in a time-division manner by performing control for alternately switching the light emission patterns of the LEDs 41 to 43 between two patterns. Therefore, with the light source apparatus 3A according to the present embodiment, for example, it is possible to cause the monitor 5 to display the simultaneous observation image including the white light observation image and the narrow band light observation image without using a wavelength switching mechanism such as a rotation filter capable of switching a state in which incident white light is directly emitted and a state in which a wavelength band of the incident white light is limited and narrow band light is emitted. Therefore, with the light source apparatus 3A according to the present embodiment, for example, it is possible to further improve, than in the past, a degree of freedom of light amount adjustment in individually adjusting brightness of the white light observation image included in the simultaneous observation image and brightness of the narrow band light observation image included in the simultaneous observation image.

With the light source apparatus 3A according to the present embodiment, in the white light observation mode, the light amount ratio RA is set such that a spectral distribution of the mixed light obtained by mixing the NGB light and the LOB light coincides with a spectral distribution of either one or the WLC light and the WLD light. The light amount adjustment for setting the light amount ratio RA and the light amount ratio RB to obtain a color balance suitable for the observation by the white light observation image is performed. Therefore, with the light source apparatus 3A according to the present embodiment, for example, in the white light observation mode, it is possible to cause the monitor 5 to display, in color reproducibility suitable for diagnosis and/or treatment and the like of a biological tissue which is irradiated with the MXC light, a white light observation image obtained by picking up an image of the biological tissue.

Third Embodiment

FIG. 16 to FIG. 28 relate to a third embodiment of the present invention.

Note that, in the present embodiment, detailed explanation concerning portions including components and the like same as the components and the like in at least one of the first and second embodiments is omitted. Portions including components and the like different from the components and the like in both of the first and second embodiments are mainly explained.

Figure 16:
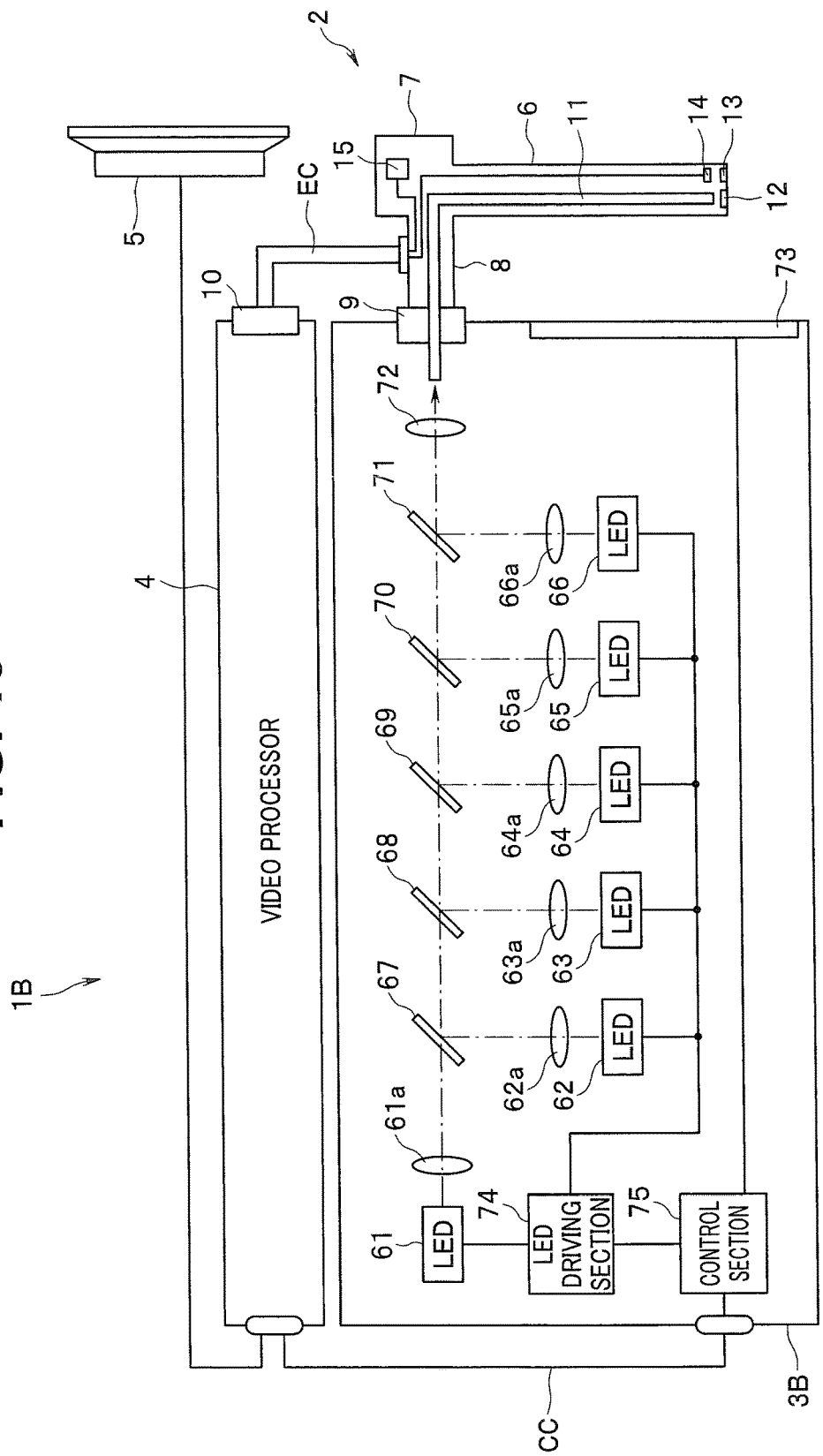
FIG. 16 is a diagram showing a configuration of a main part of an endoscope system including a light source apparatus according to a third embodiment.

An endoscope system 1B includes, as shown in FIG. 16, instead of the light source apparatus 3 in the endoscope system 1, a light source apparatus 3B configured to supply illumination light for illuminating an object to the endoscope 2. FIG. 16 is a diagram showing a configuration of a main part of an endoscope system including a light source apparatus according to the third embodiment.

The light source apparatus 3B includes an LED 61, a lens 61a configured to collect and emit light emitted from the LED 61, an LED 62, a lens 62a configured to collect and emit light emitted from the LED 62, an LED 63, a lens 63a configured to collect and emit light emitted from the LED 63, an LED 64, a lens 64a configured to collect and emit light emitted from the LED 64, an LED 65, a lens 65a configured to collect and emit light emitted from the LED 65, an LED 66, a lens 66a configured to collect and emit light emitted from the LED 66, dichroic mirrors 67 to 71, a lens 72, an operation panel 73, an LED driving section 74, and a control section 75.

Figure 17:
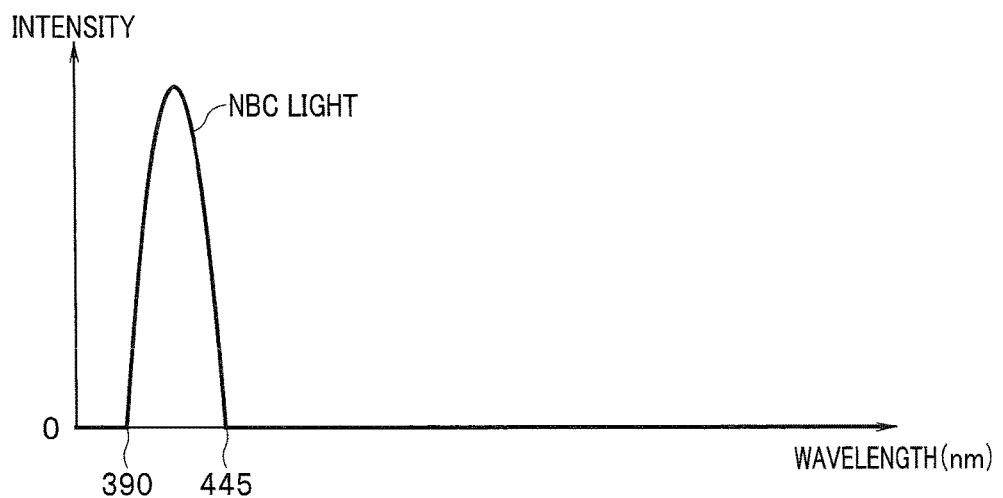
FIG. 17 is a diagram showing an example of a spectral distribution of light emitted from an LED provided in the light source apparatus according to the third embodiment.

The LED 61 is configured to emit light according to an LED driving signal supplied from the LED driving section 74. The LED 61 is configured to generate NBC light, which is narrow band light having a spectral distribution shown in FIG. 17 in, for example, a wavelength band of 390 nm to 445 nm. FIG. 17 is a diagram showing an example of a spectral distribution of light emitted from an LED provided in the light source apparatus according to the third embodiment.

Figure 18:
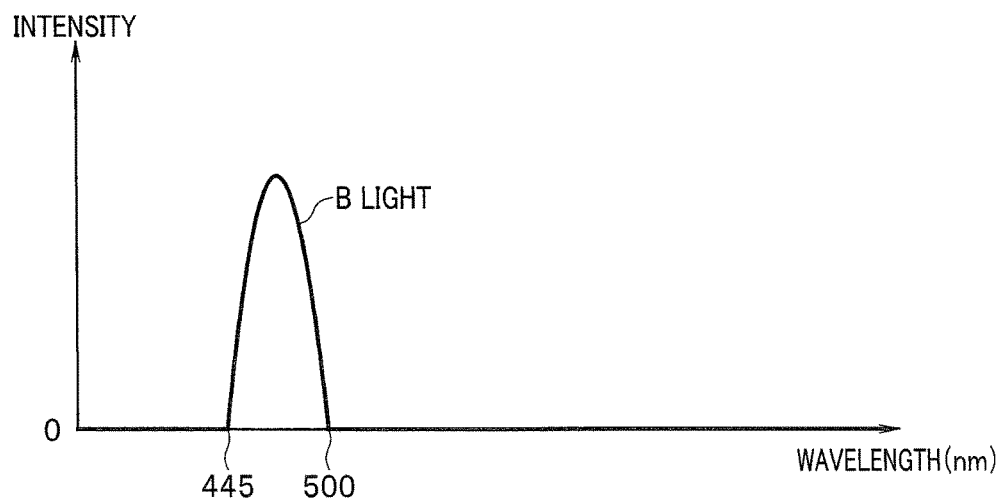
FIG. 18 is a diagram showing an example of a spectral distribution of light emitted from an LED provided in the light source apparatus according to the third embodiment.

The LED 62 is configured to emit light according to an LED driving signal supplied from the LED driving section 74. The LED 62 is configured to generate B light, which is blue light having a spectral distribution shown in FIG. 18 in, for example, a wavelength band of 445 nm to 500 nm. FIG. 18 is a diagram showing an example of a spectral distribution of light emitted from an LED provided in the light source apparatus according to the third embodiment.

Figure 19:
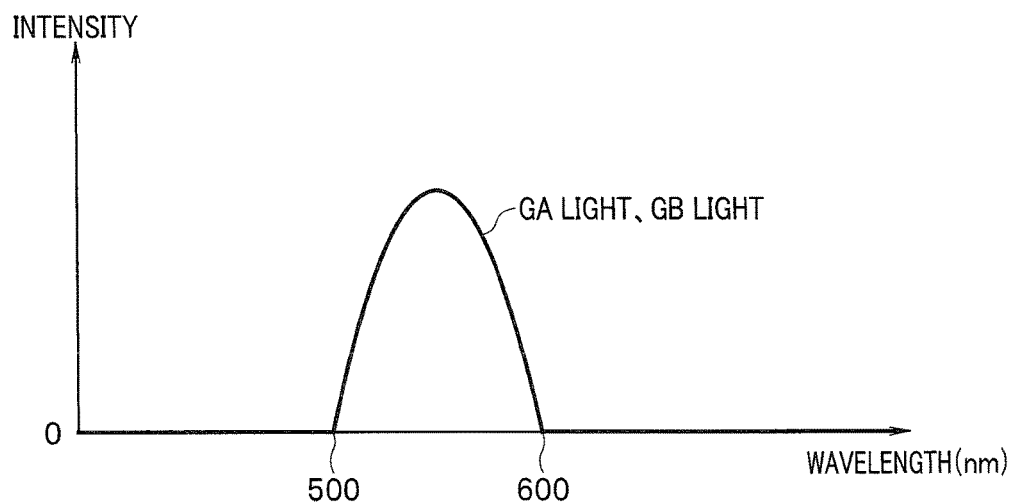
FIG. 19 is a diagram showing an example of a spectral distribution of light emitted from an LED provided in the light source apparatus according to the third embodiment.

The LED 63 is configured to emit light according to an LED driving signal supplied from the LED driving section 74. The LED 63 is configured to generate GA light, which is green light having a spectral distribution shown in FIG. 19 in, for example, a wavelength band of 500 nm to 600 nm and including a wavelength band of NGC light explained below. FIG. 19 is a diagram showing an example of a spectral distribution of light emitted from an LED provided in the light source apparatus according to the third embodiment.

The LED 64 is configured to emit light according to an LED driving signal supplied from the LED driving section 74. The LED 64 is configured to generate GB light, which is green light having a spectral distribution same as the spectral distribution of the GA light shown in FIG. 19 in, for example, the wavelength band of 500 nm to 600 nm and including the wavelength band of the NGC light explained below.

That is, in the present embodiment, the spectral distribution of the GA light and the spectral distribution of the GB light are the same.

Figure 20:
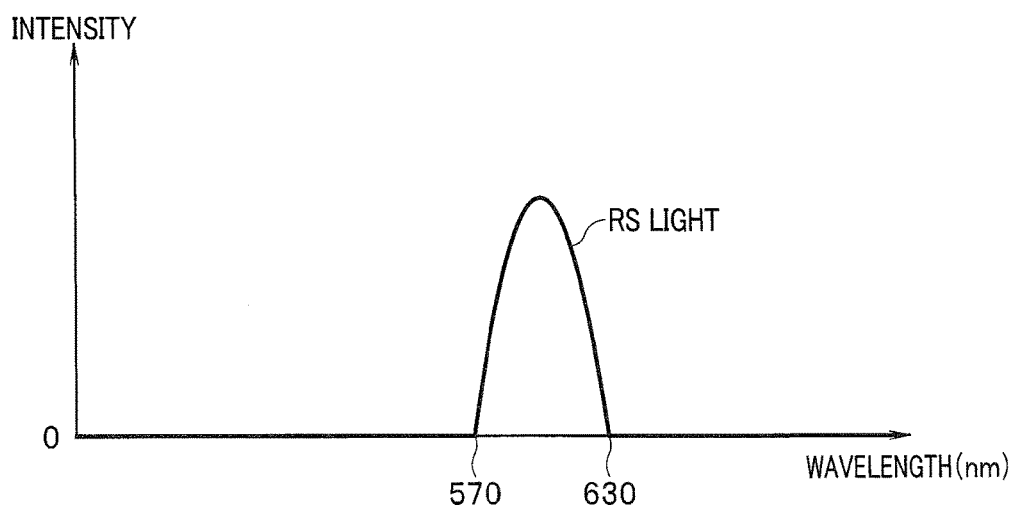
FIG. 20 is a diagram showing an example of a spectral distribution of light emitted from an LED provided in the light source apparatus according to the third embodiment.

The LED 65 is configured to emit light according to an LED driving signal supplied from the LED driving section 74. The LED 65 is configured to generate RS light, which is red light having a spectral distribution shown in FIG. 20 in, for example, a wavelength band of 570 nm to 630 nm. FIG. 20 is a diagram showing an example of a spectral distribution of light emitted from an LED provided in the light source apparatus according to the third embodiment.

Figure 21:
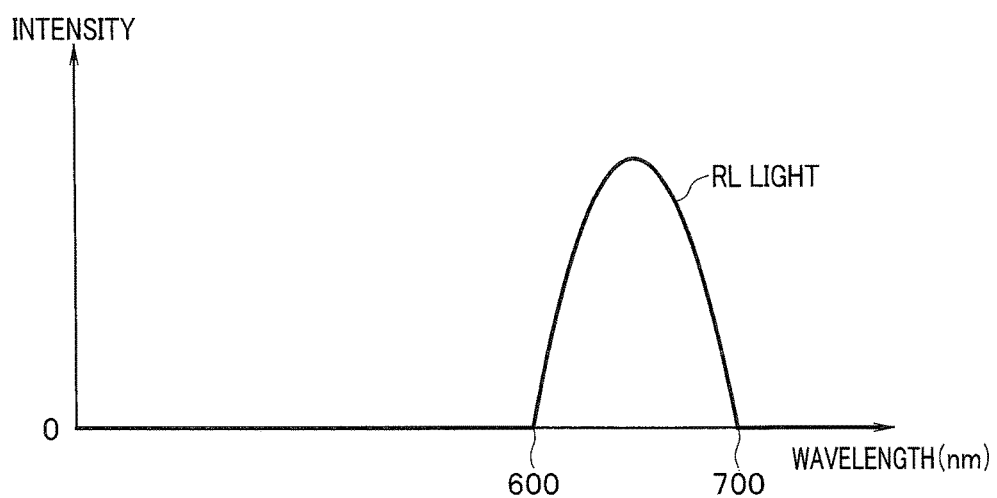
FIG. 21 is a diagram showing an example of a spectral distribution of light emitted from an LED provided in the light source apparatus according to the third embodiment.

The LED 66 is configured to emit light according to an LED driving signal supplied from the LED driving section 74. The LED 66 is configured to generate RL light, which is red light having a spectral distribution shown in FIG. 21 in, for example, a wavelength band of 600 nm to 700 nm. FIG. 21 is a diagram showing an example of a spectral distribution of light emitted from an LED provided in the light source apparatus according to the third embodiment.

Figure 22:
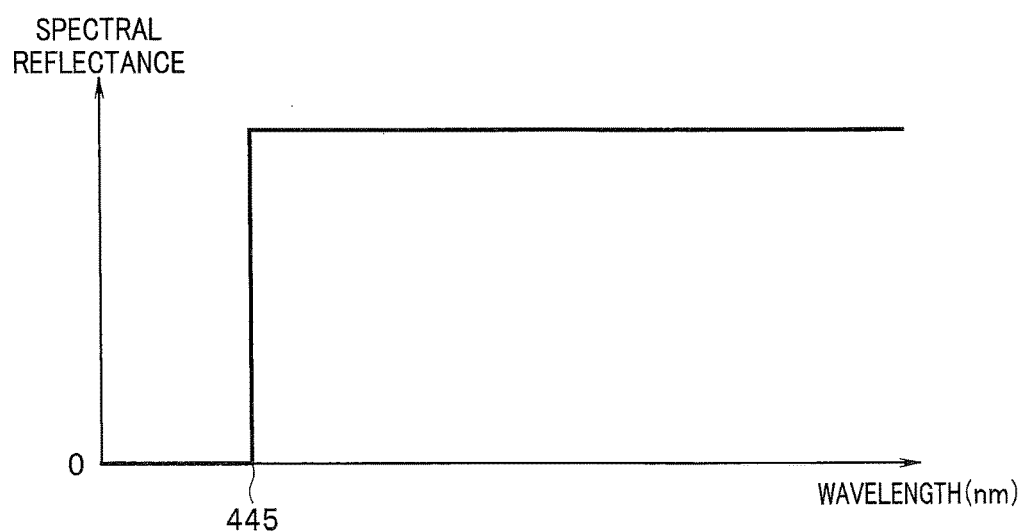
FIG. 22 is a diagram showing an example of a spectral reflection characteristic of a dichroic mirror provided in the light source apparatus according to the third embodiment.

The dichroic mirror 67 has, for example, as shown in FIG. 22, a spectral reflection characteristic for reflecting, to the connector receiver side, the B light emitted through the lens 62a. FIG. 22 is a diagram showing an example of a spectral reflection characteristic of a dichroic mirror provided in the light source apparatus according to the third embodiment.

The dichroic mirror 67 has a spectral transmission characteristic for transmitting, to the connector receiver side, the NBC light emitted through the lens 61a.

Figure 23:
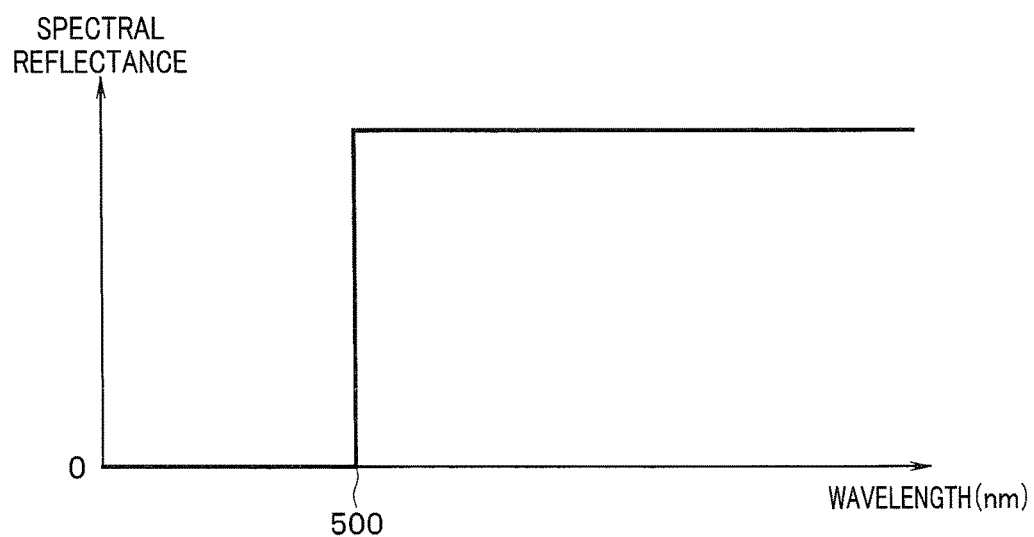
FIG. 23 is a diagram showing an example of a spectral reflection characteristic of a dichroic mirror provided in the light source apparatus according to the third embodiment.

The dichroic mirror 68 has, for example, as shown in FIG. 23, a spectral reflection characteristic for reflecting, to the connector receiver side, the GA light emitted through the lens 63a. FIG. 23 is a diagram showing an example of a spectral reflection characteristic of a dichroic mirror provided in the light source apparatus according to the third embodiment.

The dichroic mirror 68 has a spectral transmission characteristic for transmitting, to the connector receiver side, the NBC light and the B light emitted through the dichroic mirror 67.

The dichroic mirror 69 has an optical characteristic for selectively reflecting, to the connector receiver side, a part of the GB light emitted through the lens 64a, selectively transmitting, to the connector receiver side, a part of the GA light emitted through the dichroic mirror 68, and transmitting, to the connector receiver side, the NBC light and the B light emitted through the dichroic mirror 68.

Figure 24:
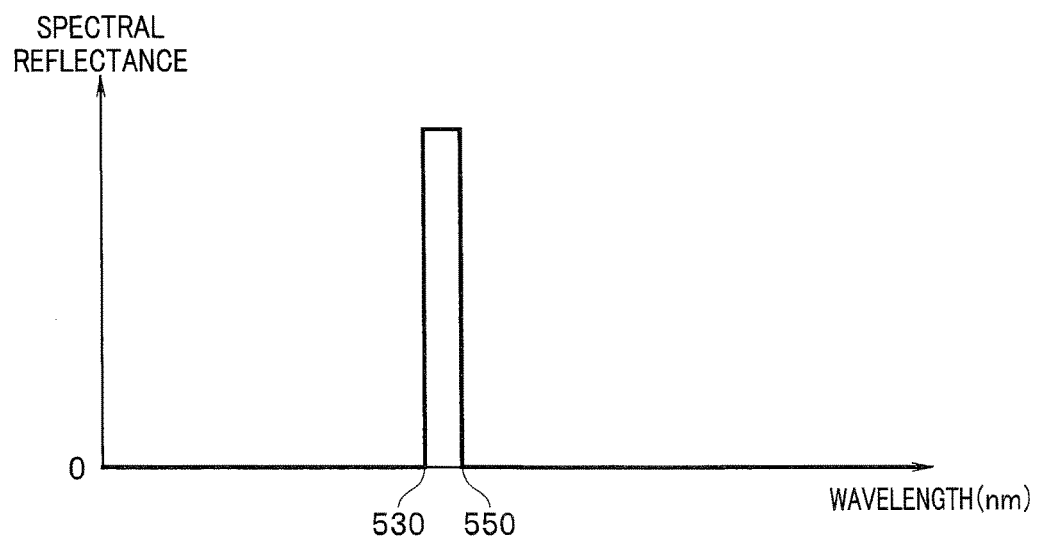
FIG. 24 is a diagram showing an example of a spectral reflection characteristic of a dichroic mirror provided in the light source apparatus according to the third embodiment.

More specifically, the dichroic mirror 69 has, for example, as shown in FIG. 24, a spectral reflection characteristic for selectively reflecting, to the connector receiver side, NGC light, which is light in a wavelength band of 530 nm to 550 nm, in the GB light emitted through the lens 64a. FIG. 24 is a diagram showing an example of a spectral reflection characteristic of a dichroic mirror provided in the light source apparatus according to the third embodiment.

The dichroic mirror 69 has a spectral transmission characteristic for selectively transmitting, to the connector receiver side, LOC light, which is light in a wavelength band other than the wavelength band of the NGC light, in the GA light emitted through the dichroic mirror 68.

That is, the dichroic mirror 69 has an optical characteristic in which a relational expression TZ+RZ=100% holds between spectral transmittance TZ in a predetermined wavelength included in a wavelength band of the GA light or the GB light and spectral reflectance RZ in the predetermined wavelength. The dichroic mirror 69 is configured as an optical member configured to extract NGC light from the GB light, extract LOC light from the GA light, and mix and output the NGC light and the LOC light.

Figure 25:
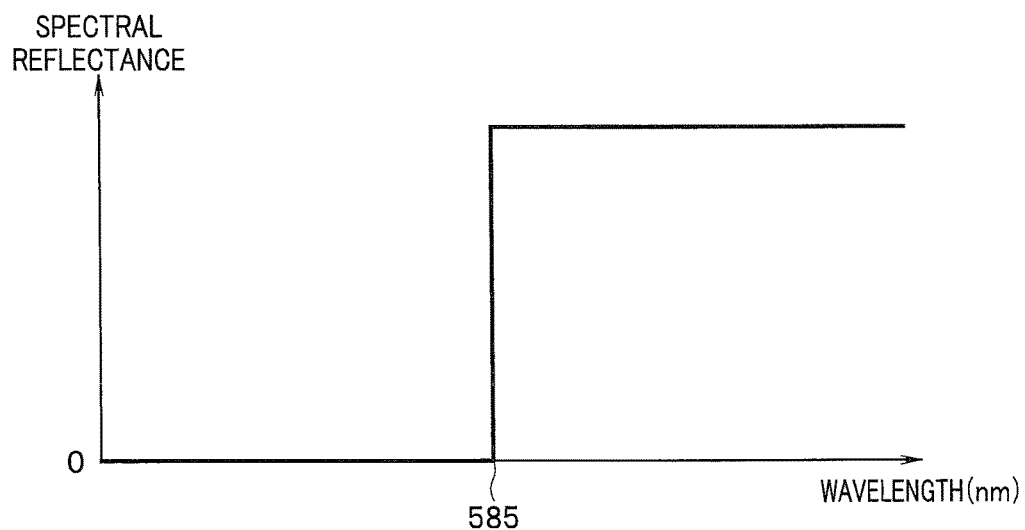
FIG. 25 is a diagram showing an example of a spectral reflection characteristic of a dichroic mirror provided in the light source apparatus according to the third embodiment.

The dichroic mirror 70 has, for example, as shown in FIG. 25, a spectral reflection characteristic for reflecting, to the connector receiver side, RSA light, which is light of 585 nm to 630 nm, equivalent to a part of the RS light emitted through the lens 65a. FIG. 25 is a diagram showing an example of a spectral reflection characteristic of a dichroic mirror provided in the light source apparatus according to the third embodiment.

The dichroic mirror 70 has a spectral transmission characteristic for transmitting, to the connector receiver side, LOD light and NGC light, which are lights in a wavelength band smaller than 585 nm, in the NBC light, the B light, and the LOC light emitted through the dichroic mirror 69.

Figure 26:
FIG. 26 is a diagram showing an example of a spectral reflection characteristic of a dichroic mirror provided in the light source apparatus according to the third embodiment.

The dichroic mirror 71 has, for example, as shown in FIG. 26, a spectral reflection characteristic for reflecting, to the connector receiver side, RLA light, which is light of 615 nm to 700 nm, equivalent to a part of the RL light emitted through the lens 66a. FIG. 26 is a diagram showing an example of a spectral reflection characteristic of a dichroic mirror provided in the light source apparatus according to the third embodiment.

The dichroic mirror 71 has a spectral transmission characteristic for transmitting, to the connector receiver side, RSB light, which is light of 585 nm to 615 nm, equivalent to a part of the NBC light, the B light, the NGC light, the LOD light, and the RSA light emitted through the dichroic mirror 70.

The lens 72 is configured to collect the respective lights emitted through the dichroic mirror 71 and emit the lights to a light incident surface of the light guide 11 disposed near the connector receiver according to connection of the optical connector 9.

The operation panel 73 includes user interfaces such as a power supply switch (not shown in the figure) for enabling a user to perform operation related to switching of ON/OFF of a power supply and an observation mode selection switch (not shown in the figure) for enabling operations for selecting a desired observation mode out of a plurality of observation modes.

The LED driving section 74 is configured to generate and output, according to control by the control section 75, LED driving signals for respectively driving the LEDs 61 to 66.

The control section 75 is configured to perform, according to operation performed in the observation mode selection switch of the operation panel 73, on the LED driving section 74, control for individually setting light emission states of the LEDs 61 to 66. The control section 75 is configured to perform, on the basis of a light amount adjustment signal outputted from the video processor 4 via the communication cable CC, on the LED driving section 74, control for respectively adjusting light amounts of the NBC light, the B light, the GA light, the GB light, the RS light, and the RL light.

Operation and the like of the endoscope system 1B including the light source apparatus 3B according to the present embodiment are explained.

For example, after connecting the respective sections of the endoscope system 1B and turning on the power supply, the user such as a surgeon performs operation for selecting a white light observation mode in the observation mode selection switch of the operation panel 73.

When detecting that the operation for selecting the white light observation mode is performed in the observation mode selection switch of the operation panel 73, the control section 75 performs, on the LED driving section 74, control for causing the LEDs 61 to 66 to simultaneously emit lights.

Figure 27:
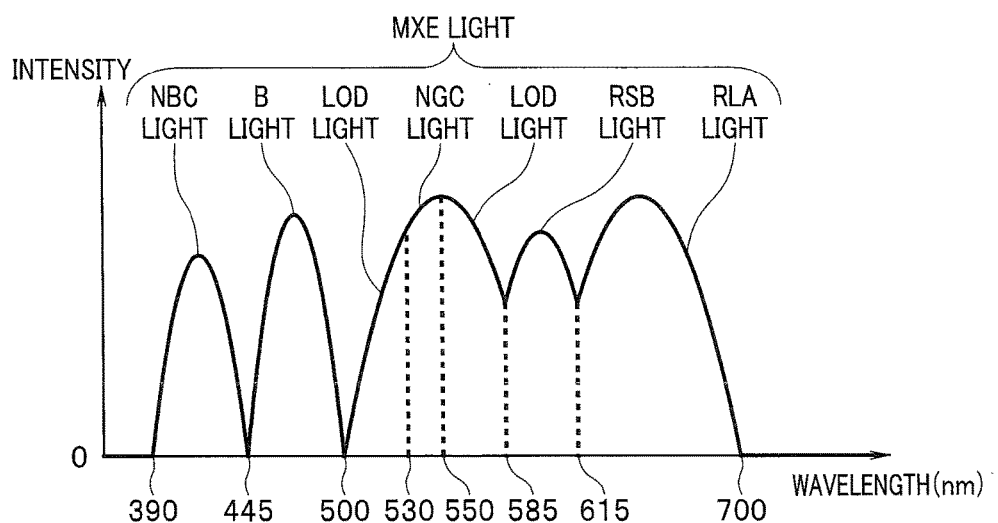
FIG. 27 is a diagram showing an example of a spectral distribution of illumination light emitted from the light source apparatus according to the third embodiment when the white light observation mode is selected.

According to the control by the control section 75 explained above, the GB light emitted from the LED 64 is separated into NGC light according to the spectral reflection characteristic of the dichroic mirror 69, the GA light emitted from the LED 63 is separated into LOC light according to the spectral transmission characteristic of the dichroic mirror 69, and MXE light, which is mixed light obtained by mixing, with the dichroic mirror 71, the NBC light emitted from the LED 61, the B light emitted from the LED 62, LOD light equivalent to a part of the LOC light, the NGC light, RSB light equivalent to a part of the RS light emitted from the LED 65, and RLA light equivalent to a part of the RL light emitted from the LED 66, is supplied to the endoscope 2 as illumination light. That is, the MXE light, which is white light, supplied from the light source apparatus 3B as the illumination light of the white light observation mode has a spectral distribution illustrated in FIG. 27. FIG. 27 is a diagram showing an example of a spectral distribution of illumination light emitted from the light source apparatus according to the third embodiment when the white light observation mode is selected. Note that it is assumed that a spectral distribution of the NBC light shown in FIG. 27 indicates an example of a spectral distribution at a time when light amount adjustment is performed to obtain a light amount suitable for observation by a white light observation image.

According to the control by the control section 75 explained above, an optical image of the object illuminated by the MXE light is picked up by the image sensor 14 and a white light observation image generated according to an image pickup signal outputted from the image sensor 14 is displayed on the monitor 5 on a frame-by-frame basis.

On the other hand, for example, after disposing the insertion section 6 in a position where a desired biological tissue present in the body cavity of the subject can be visually recognized by the white light observation image, the user performs, in the observation mode selection switch of the operation panel 73, operation for selecting a narrow band light observation mode included in one kind of the special light observation mode.

When detecting that the operation for selecting the narrow band light observation mode is performed in the observation mode selection switch of the operation panel 73, the control section 75 performs, on the LED driving section 74, control for extinguishing the LEDs 62, 63, and 65 while causing the LEDs 61 and 64 to simultaneously emit lights.

Figure 28:
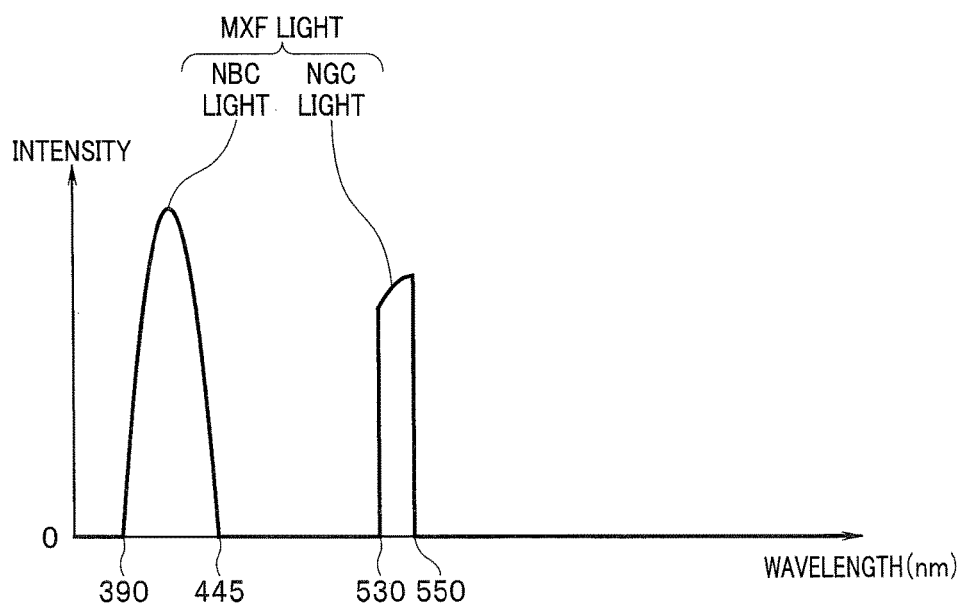
FIG. 28 is a diagram showing an example of a spectral distribution of illumination light emitted from the light source apparatus according to the third embodiment when the narrow band light observation mode is selected.

According to the control by the control section 75 explained above, the GB light emitted from the LED 64 is separated into NGC light according to the spectral reflection characteristic of the dichroic mirror 69 and MXF light, which is mixed light obtained by mixing, with the dichroic mirror 71, NBC light emitted from the LED 61 and the NGC light, is supplied to the endoscope 2 as illumination light. That is, the MXF light, which is special light supplied from the light source apparatus 3B as the illumination light of the narrow band light observation mode, is light narrower in a band than the MXE light and has a spectral distribution illustrated in FIG. 28. FIG. 28 is a diagram showing an example of a spectral distribution of illumination light emitted from the light source apparatus according to the third embodiment when the narrow band light observation mode is selected.

According to the control by the control section 75 explained above, an optical image of a desired biological tissue illuminated by the MXF light is picked up by the image sensor 14 and a narrow band light observation image generated according to an image pickup signal outputted from the image sensor 14 is displayed on the monitor 5 on a frame-by-frame basis.

Note that, in the present embodiment, it may also be possible to select, as a special light observation mode, other observation modes different from the narrow band light observation mode such as an autofluorescence observation mode for observing fluorescent light emitted by exciting a fluorescent substance included in a biological tissue and a large-diameter blood vessel observation mode for observing a blood vessel having a large diameter present in the biological tissue. With the configuration of the light source apparatus 3B according to the present embodiment, for example, when the autofluorescence observation mode is selected, the control section 75 only has to perform control for extinguishing the LEDs 62, 63, and 65 while causing the LEDs 61 and 64 to simultaneously emit lights. With the configuration of the light source apparatus 3B according to the present embodiment, for example, when a deep blood vessel observation mode is selected, the control section 75 only has to perform control for extinguishing the LEDs 61 and 62 while causing the LEDs 63 to 66 to simultaneously emit lights.

According to the present embodiment, as long as the MXE light is supplied as the illumination light for obtaining the white light observation image and the MXF light is supplied as the illumination light for obtaining the narrow band light observation image, the dichroic mirror 69 may be configured as an optical member configured to extract NGC light from the GA light, extract LOC light from the GB light, and mix and emit the NGC light and the LOC light. In such a configuration, when the white light observation mode is selected, the control section 75 may perform control for causing the LEDs 61 to 66 to simultaneously emit lights and, when the narrow band light observation mode is selected, the control section 75 may perform control for causing the LEDs 61 and 63 to simultaneously emit lights.

According to the embodiment, for example, when the simultaneous observation mode is selected, by performing control for irradiating the object with the MXE light and the MXF light in a time-division manner, the control section 75 can cause the monitor 5 to display a simultaneous observation image same as the simultaneous observation image in the second embodiment.

The present embodiment is not limited to be applied when spectral distributions of the GA light and the GB light are completely the same and is also applied when the spectral distributions of the GA light and the GB light are substantially the same.

As explained above, with the light source apparatus 3B according to the present embodiment, with a simple configuration for switching the light emission states of the LEDs 61 to 66 according to the observation mode selected in the observation mode selection switch of the operation panel 73, it is possible to supply the MXE light to the endoscope 2 as the illumination light of the white light observation mode. It is possible to supply the MXF light to the endoscope 2 as the illumination light of the narrow band light observation mode. Therefore, with the light source apparatus 3B according to the present embodiment, it is possible to further simplify a configuration for performing the white light observation and the special light observation than in the past.

Note that the present invention is not limited to the respective embodiments explained above. It goes without saying that various changes and applications are possible within a range not departing from the spirit of the invention.

What is claimed is:

1. A light source apparatus capable of irradiating an object alternately in a time-division manner with, as illumination light for illuminating the object, white light for obtaining a white light observation image and a light of a predetermined wavelength band for obtaining a narrow band light observation image, which is narrower in a band than the white light, the light source apparatus comprising:
   a first light source configured to emit light in a first wavelength band which includes the light in the predetermined wavelength band;
   a second light source configured to emit light in a second wavelength band which includes the light in the predetermined wavelength band;
   an optical member configured to selectively transmit light in the predetermined wavelength band included in the light in the first wavelength band, and selectively reflect light in a third wavelength band, which is light in a wavelength band other than the predetermined wavelength band included in the second wavelength band; and
   a controller configured to alternately repeat:
      first control of irradiating the object with the white light mixed with the light in the predetermined wavelength band emitted through the optical member and the light in the third wavelength band as the illumination light by causing the first light source and the second light source to simultaneously emit light, and
      second control of irradiating the object with the light in the predetermined wavelength band emitted through the optical member as the illumination light by causing the first light source to emit light and causing the second light source to stop emitting light.

2. The light source apparatus according to claim 1, wherein a spectral distribution of the light in the first wavelength band and a spectral distribution of the light in the second wavelength band are same.

3. The light source apparatus according to claim 1, wherein both of the first light source and the second light source are solid-state light sources.

4. The light source apparatus according to claim 1, wherein at least one wavelength band of a green wavelength band and a blue wavelength band is included in the predetermined wavelength band.

5. The light source apparatus according to claim 1, wherein the first light source is configured to emit the white light as the light in the first wavelength band, and the second light source is configured to emit the white light as the light in the second wavelength band.

* * * * *